(12) United States Patent
Triebel

(10) Patent No.: US 12,214,012 B2
(45) Date of Patent: *Feb. 4, 2025

(54) COMBINED PREPARATIONS FOR THE TREATMENT OF CANCER

(71) Applicant: IMMUTEP S.A.S., Orsay (FR)

(72) Inventor: Frederic Triebel, Versailles (FR)

(73) Assignee: IMMUTEP S.A.S., Saint-Aubin (FR)

( * ) Notice: Subject to any disclaimer, the term of this patent is extended or adjusted under 35 U.S.C. 154(b) by 865 days.

This patent is subject to a terminal disclaimer.

(21) Appl. No.: 16/918,527

(22) Filed: Jul. 1, 2020

(65) Prior Publication Data

US 2020/0323957 A1  Oct. 15, 2020

Related U.S. Application Data

(63) Continuation of application No. 15/105,789, filed as application No. PCT/EP2014/078779 on Dec. 19, 2014, now Pat. No. 10,736,940.

(30) Foreign Application Priority Data

Dec. 19, 2013 (GB) .................................... 1322626

(51) Int. Cl.
| | |
|---|---|
| A61K 38/17 | (2006.01) |
| A61K 31/282 | (2006.01) |
| A61K 31/4745 | (2006.01) |
| A61K 31/555 | (2006.01) |
| A61K 45/06 | (2006.01) |
| C07K 14/705 | (2006.01) |

(52) U.S. Cl.
CPC ........ *A61K 38/1774* (2013.01); *A61K 31/282* (2013.01); *A61K 31/4745* (2013.01); *A61K 31/555* (2013.01); *A61K 45/06* (2013.01); *C07K 14/70503* (2013.01); *C07K 2319/30* (2013.01)

(58) Field of Classification Search
CPC .......... C07K 14/70503; C07K 2319/30; A61K 38/1774; A61K 31/282; A61K 2300/00; A61K 45/06; A61P 35/00; A61P 35/02; A61P 35/04

See application file for complete search history.

(56) References Cited

U.S. PATENT DOCUMENTS

| | | | |
|---|---|---|---|
| 5,078,996 A | 1/1992 | Conlon, III et al. |
| 5,098,702 A | 3/1992 | Zimmerman et al. |
| 5,225,348 A | 7/1993 | Nagata et al. |
| 5,266,491 A | 11/1993 | Nagata et al. |
| 5,436,146 A | 7/1995 | Shenk et al. |
| 5,539,084 A | 7/1996 | Geysen |
| 5,637,483 A | 6/1997 | Dranoff et al. |
| 5,665,577 A | 9/1997 | Sodroski et al. |
| 5,700,907 A | 12/1997 | Hercend et al. |
| 5,753,500 A | 5/1998 | Shenk et al. |
| 5,773,578 A | 6/1998 | Hercend et al. |
| 5,785,973 A | 7/1998 | Bixler et al. |
| 5,798,231 A | 8/1998 | Hercend et al. |
| 5,817,511 A | 10/1998 | Hercend et al. |
| 5,830,758 A | 11/1998 | Hercend et al. |
| 5,840,839 A | 11/1998 | Wang et al. |
| 5,872,005 A | 2/1999 | Wang et al. |
| 5,874,250 A | 2/1999 | Hercend et al. |
| 5,904,920 A | 5/1999 | Dranoff et al. |
| 5,955,300 A | 9/1999 | Faure et al. |
| 5,955,331 A | 9/1999 | Danos et al. |
| 5,976,877 A | 11/1999 | Hercend et al. |
| 5,981,276 A | 11/1999 | Sodroski et al. |
| 5,985,290 A | 11/1999 | Jaffee et al. |
| 6,033,674 A | 3/2000 | Jaffee et al. |
| 6,037,177 A | 3/2000 | Snyder |
| 6,040,183 A | 3/2000 | Ferrari et al. |
| 6,093,570 A | 7/2000 | Ferrari et al. |
| 6,114,516 A | 9/2000 | Hercend et al. |
| 6,143,273 A | 11/2000 | Faure et al. |
| 6,277,368 B1 | 8/2001 | Hiserodt et al. |
| 6,350,445 B1 | 2/2002 | Jaffee et al. |
| 6,410,509 B1 | 6/2002 | Triebel |
| 6,428,953 B1 | 8/2002 | Naldini et al. |
| 6,464,973 B1 | 10/2002 | Levitsky et al. |
| 6,482,925 B1 | 11/2002 | El Tayar et al. |
| 6,506,604 B2 | 1/2003 | Finer et al. |
| 6,596,536 B1 | 7/2003 | Hercend et al. |

(Continued)

FOREIGN PATENT DOCUMENTS

| | | |
|---|---|---|
| CA | 2 391 927 A1 | 5/2001 |
| CN | 101873864 | 10/2010 |

(Continued)

OTHER PUBLICATIONS

Pollaro and Heinis (Med Chem Commun., 2010, vol. 1, pp. 319-324 (Year: 2010).*
Pinto et al (Cancer Chemotherapy and Pharmacology, 2011, vol. 67, pp. 275-284) (Year: 2011).*
Aguilar et al (Journal of Cellular Biochemistry, 2011, vol. 112, pp. 1969-1977) (Year: 2011).*
Schlom et al (Clinical Cancer Research, 2007, vol. 13, pp. 3776-3782) (Year: 2007).*
The abstract of Ruggiero et al (Anticancer Drugs, 2013, vol. 24, pp. 1007-1019) (Year: 2013).*

(Continued)

*Primary Examiner* — Karen A. Canella

(74) *Attorney, Agent, or Firm* — Scully, Scott, Murphy & Presser, P.C.

(57) ABSTRACT

Combined preparations for the treatment of cancer are described. The combined preparations comprise: (a) LAG-3 protein, or a derivative thereof that is able to bind to MHC class II molecules; and (b) an anti-neoplastic agent, wherein the anti-neoplastic agent is a platinum-based anti-neoplastic agent or a topoisomerase I inhibitor. Methods for the treatment of cancer using the combined preparations are also described.

12 Claims, 12 Drawing Sheets

Specification includes a Sequence Listing.

(56) References Cited

U.S. PATENT DOCUMENTS

| | | | |
|---|---|---|---|
| RE38,313 E | 11/2003 | Faure et al. | |
| 6,855,802 B1 | 2/2005 | Triebel et al. | |
| 6,875,844 B1 | 4/2005 | Ronsin et al. | |
| 7,109,026 B2 | 9/2006 | Triebel | |
| 7,294,712 B2 | 11/2007 | Hercend et al. | |
| 8,425,897 B2 | 4/2013 | Jooss et al. | |
| 9,220,776 B2 | 12/2015 | Sharma et al. | |
| 9,579,382 B2 | 2/2017 | Triebel | |
| 10,232,038 B2 | 3/2019 | Triebel | |
| 10,736,940 B2 | 8/2020 | Triebel | |
| 10,874,713 B2 | 12/2020 | Triebel et al. | |
| 10,940,181 B2 | 3/2021 | Triebel et al. | |
| 2002/0192195 A1 | 12/2002 | Triebel | |
| 2004/0081686 A1 | 4/2004 | Kravtzoff et al. | |
| 2004/0171551 A1 | 9/2004 | Triebel | |
| 2004/0197312 A1 | 10/2004 | Moskalenko et al. | |
| 2006/0110755 A1 | 5/2006 | Duke et al. | |
| 2006/0127482 A1* | 6/2006 | Fewell | A61K 31/17 514/45 |
| 2007/0231298 A1 | 10/2007 | Li et al. | |
| 2008/0003235 A1 | 1/2008 | Triebel | |
| 2008/0069770 A1 | 3/2008 | Hercend et al. | |
| 2009/0130054 A1 | 5/2009 | Jooss et al. | |
| 2011/0008331 A1 | 1/2011 | Triebel | |
| 2011/0150892 A1 | 6/2011 | Thudium et al. | |
| 2013/0109843 A1 | 5/2013 | Carven et al. | |
| 2013/0309250 A1 | 11/2013 | Cogswell et al. | |
| 2014/0341920 A1 | 11/2014 | Noelle | |
| 2016/0310570 A1 | 10/2016 | Triebel | |
| 2017/0119876 A1 | 5/2017 | Triebel | |
| 2018/0271940 A1 | 9/2018 | Triebel et al. | |
| 2020/0323957 A1 | 10/2020 | Triebel | |

FOREIGN PATENT DOCUMENTS

| | | |
|---|---|---|
| CN | 104185681 A | 12/2014 |
| EA | 0 03 740 B1 | 7/1998 |
| EP | 0 252 741 A2 | 1/1988 |
| EP | 1 537 878 A1 | 6/2005 |
| EP | 2 044 949 A1 | 4/2009 |
| EP | 2 087 891 A2 | 8/2009 |
| EP | 3 089 749 B1 | 12/2014 |
| JP | H05009131 A | 1/1993 |
| JP | 2006-124383 A | 5/2006 |
| JP | 2006-141346 A | 6/2006 |
| JP | 2010-540616 A | 12/2010 |
| JP | 2012-500006 A | 1/2012 |
| JP | 2013-126999 A | 6/2013 |
| JP | 2014-510016 A | 4/2014 |
| JP | 2017-503014 A | 1/2017 |
| KR | 10-2011-0050507 | 5/2011 |
| WO | 92/05262 A1 | 4/1992 |
| WO | 96/40210 A1 | 12/1996 |
| WO | 98/23741 A1 | 6/1998 |
| WO | 98/23748 A1 | 6/1998 |
| WO | 98/46728 A1 | 10/1998 |
| WO | 99/38954 A1 | 8/1999 |
| WO | 00/72686 A1 | 12/2000 |
| WO | 01/035989 A2 | 5/2001 |
| WO | 2005/035779 A2 | 4/2005 |
| WO | 2005/103079 A1 | 11/2005 |
| WO | 2007/126805 A2 | 11/2007 |
| WO | 2007/150077 A2 | 12/2007 |
| WO | 2008/156712 A1 | 12/2008 |
| WO | 2009/032256 A2 | 3/2009 |
| WO | 2009/044273 A2 | 4/2009 |
| WO | 2010/019570 A2 | 2/2010 |
| WO | 2012/075679 A1 | 6/2012 |
| WO | 2013/173223 A1 | 11/2013 |
| WO | 2014/194293 A1 | 12/2014 |
| WO | 2015/042246 A1 | 3/2015 |
| WO | 2015/112900 A1 | 7/2015 |
| WO | 2015/131176 A1 | 9/2015 |
| WO | 2015/200119 A1 | 12/2015 |

OTHER PUBLICATIONS

Albert R. K. et al., "The Merck Manual of Diagnosis and Therapy 18th Edition", Merck Research Laboratories, pp. 1160-1167 (2006).
Altschul S.F. et al., "Basic Local Alignment Search Tool", J. Mol. Biol. 215:403-410 (1990).
Altschul S.F. et al., "Gapped BLAST and PSI-BLAST: A New Generation of Protein Database Search Programs", Nucleic Acids Research 25(17):3389-3402 (1997).
Andreae S. et al., "MHC Class II Signal Transduction in Human Dendritic Cells Induced by a Natural Ligant, the LAG-3 Protein (CD223)", Blood 102(6):2130-2137 (2003).
Aoki T. et al., "Expression of Murine Interleukin 7 in a Murine Glioma Cell Line Results in Reduced Tumorigenicity In Vivo", Proc. Natl. Acad. Sci. USA 89:3850-3854 (May 1992).
Armand P. et al., "Disabling Immune Tolerance by Programmed Death-1 Blockade With Pidilizumab After Autologous Hematopoietic Stem-Cell Transplantation for Diffuse Large B-Cell Lymphoma: Results of an International Phase II Trial", Journal of Clinical Oncology 31(33):4199-4206 (Nov. 20, 2013).
Armstrong T.D. et al., "Cytokine Modified Tumor Vaccines", Surg. Oncology Clin. N. Am. 11:681-696 (2002).
Asher A.L. et al., "Murine Tumor Cells Transduced With the Gene for Tumor Necrosis Factor-α", J. Immunol. 146:3227-3234 (1991).
Barber D.L. et al., "Restoring Function in Exhausted CD8 T Cells During Chronic Viral Infection", Nature 439:682-687 (Feb. 2006).
Benson Jr. D.M. et al., "The PD-1/PD-L1 Axis Modulates the Natural Killer Cell Versus Multiple Myeloma Effect: A Therapeutic Target for CT-011, a Novel Monoclonal Anti-PD-1 Antibody", Blood 116(13):2286-2294 (Sep. 30, 2010).
Berkelhammer J. et al., "Development of a New Melanoma Model in C57BL/6 Mice", Cancer Research 42:3157-3163 (Aug. 1982).
Blackburn, S.D. et al., "Coregulation of CD8+ T cell Exhaustion by Multiple Inhibitory Receptors During Chronic Viral Infection", Nature Immunology 10(1):29-37 (Nov. 30, 2008).
Blackburn S.D. et al., "Selective Expansion of a Subset of Exhausted CD8 T Cells by αPD-L1 Blockade", PNAS 105(39):15016-15021 (Sep. 30, 2008).
Blank C. et al., "Blockade of PD-L1 (B7-H1) Augments Human Tumor-Specific T Cell Responses In Vitro", Int. J. Cancer 119:317-327 (2006).
Blattman J.N. et al., "Impact of Epitope Escape on PD-1 Expression and CD8 T-Cell Exhaustion During Chronic Infection", Journal of Virology 83(9):4386-4394 (May 2009).
Bock S.N. et al., "Biological and Antitumor Effects of Recombinant Human Macrophage Colony-Stimulating Factor in Mice", Cancer Research 51:2649-2654 (May 15, 1991).
Bodey B. et al., "Failure of Cancer Vaccines: The Significant Limitations of this Approach to Immunotherapy", Anticancer Research 20:2665-2676 (2000), Abstract.
Boon T., "Toward a Genetic Analysis of Tumor Rejection Antigens", Advances in Cancer Research 58:177-210 (1992).
Brendel E. et al., "Pharmacokinetic Results of a Phase I Trial of Sorafenib in Combination With Dacarbazine in Patients With Advanced Solid Tumors", Cancer Chemother Pharmacol 68:53-61 (2011).
Brignone C. et al., "First-Line Chemoimmunotherapy in Metastatic Breast Carcinoma: Combination of Paclitaxel and IMP321 (LAG-3Ig) Enhances Immune Responses and Antitumor Activity", Journal of Translational Medicine 8(1):71 (Jul. 23, 2010).
Brignone C. et al., "A Phase I Pharmacokinetic and Biological Correlative Study of IMP321, a Novel MHC Class II Agonist, in Patients With Advanced Renal Cell Carcinoma", Cancer Therapy: Clinical 15(19):6225-6231 (Oct. 1, 2009).
Brignone C. et al., "IMP321 (SLAG-3) Safety and T Cell Response Potentiation Using an Influenza Vaccine as a Model Antigen: A Single-Blind Phase I Study", Vaccine 25:4641-4650 (2007).
Brignone C. et al., "A Soluble Form of Lyphocyte Activation Gene-3 (IMP321) Induces Activation of a Large Range of Human Effector Cytotoxic Cells", The Journal of Immunology 179:4202-4211 (2007).
Brignone C. et al., "IMP321 (sLAG-3), an Immunopotentiator for T Cell Responses Against a HBsAg Antigen in Healthy Adults: a

(56) References Cited

OTHER PUBLICATIONS

Single Blind Randomised Controlled Phase I Study", Journal of Immune Based Therapies and Vaccines 5:5:15 pages (2007).
Brown J.A. et al., "Blockade of Programmed Death-1 Ligands on Dendritic Cells Enhances T Cell Activation and Cytokine Production", The Journal of Immunology 170:1257-1266 (2003).
Bukowski R.M. et al., "Phase I Trial of Subcutaneous Recombinant Macrophage Colony-Stimulating Factor: Clinical and Immunomodulatory Effects", Journal of Clinical Oncology 12(1):97-106 (1994).
Buisson S. et al., "LAG-3 (CD223) Reduces Macrophage and Dendritic Cell Differentiation from Monocyte Precursors", Immunology 114:369-374 (2005).
Campanella J.J. et al., "MatGAT: An Application that Generates Similarity/Identity Matrices Using Protein or DNA Sequences", BMC Bioinformatics 4:29 (2003).
Cantrell M.A. et al., "Cloning, Sequence, and Expression of a Human Granulocyte/Macrophage Colony-Stimulating Factor", Proc. Natl. Acad. Sci. USA 82:6250-6254 (Sep. 1985).
Cao D. et al., "Intrahepatic Expression of Programmed Death-1 and its Ligands in Patients with HBV-Related Acute-on-Chronic Liver Failure", Inflammation 36(1):110-120 (Feb. 2013).
Casati C. et al., "Soluble Human LAG-3 Molecule Amplifies the In Vitro Generation of Type 1 Tumor-Specific Immunity", Cancer Research 66(8):4450-4460 (Apr. 15, 2006).
Castellino F. et al., "Chemokines Enhance Immunity by Guiding Naive CD8+ T Cells to Sites of CD4+ T Cell-Dendritic Cell Interaction", Nature 440:890-895 (Apr. 13, 2006).
Chang A.E. et al., "Immunogenetic Therapy of Human Melanoma Utilizing Autologous Tumor Cells Transduced to Secrete Granulocyte-Macrophage Colony-Stimulating Factor", Human Gene Therapy 11:839-850 (Apr. 10, 2000).
Chaux P. et al., "Estimation of the Frequences of Anti-Mage-3 Cytolytic T-Lymphocyte Precursors in Blood from Individuals Without Cancer", Int. J. Cancer 77:538-542 (1998).
Collins J.L., et al. "The Anitcancer Drug, Cisplatin, Increases the Naturally Occuring Cell-Mediated Lysis of Tumor Cells", Canceler Immunology Immunotherapy 29:17-22 (May 1989).
Collins J.L., et al. "Humans Express Natural Cytotoxic (NC) Cell Activity that is Similar to Murine NC Cell Activity", 138(12):4180-4184 (Jun. 15, 1987).
Commandone A. et al., "High Dose Methotrexate in Adult Patients With Osteosarcoma: Clinical and Pharmacokinetic Results", Acta Oncologica 44:406-411 (2005).
Cukier-Meisner E. "Walking the Toll Road", BioCentury, Product Development, p. 3 only (2014).
Curiel T.J. et al., "Blockade of B7-H1 Improves Myeloid Dendritic Cell-Mediated Antitumor Immunity", Nature Medicine 9(5):562-567 (May 2003).
Darrow T.L. et al., "The Role of HLA Class I Antigens in Recognition of Melanoma Cells by Tumor-Specific Cytotoxic T Lymphocytes", 142:3329-3335 (1989).
Dicarlo E. et al., "Immunological Mechanisms Elicited at the Tumour Site by Lymphocyte Activation Gene-3 (LAG-3) Versus IL-12; Sharing a Common Th1 Anti-Tumour Immune Pathway", Journal of Pathology GB 205:82-91 (2005).
Dienz O. et al., "The Effects of IL-6 on CD4 T Cell Responses", Clin Immunol. 130(1):27-33 (Jan. 2009).
Dong H. et al., "Tumor-Associated B7-H1 Promotes T-Cell Apoptosis: A Potential Mechanism of Immune Evasion", Nature Medicine 8(8):793-800 (Aug. 2002).
Dorner B.G. et al., "MIP-1a, MIP-1B, Rantes, and ATAC/Lymphotactin Function Together With IFN-y as Type 1 Cytokines", PNAS 99(9):6181-6186 (Apr. 30, 2012).
Dranoff G. et al., "Vaccination with Irradiated Tumor Cells Engineered to Secrete Murine Granulocyte-Macrophage Colony-Stimulating Factor Stimulates Potent, Specific, and Long-Lasting Anti-Tumor Immunity", Proc. Natl. Acad. Sci. USA 90:3539-3543 (Apr. 1993).
Dummer R. et al., "GVAX Cell Genesys", Current Opinion in Investigational Drugs 2(6):844-848 (2001), Abstract.

El Mir S. et al., "A Soluble Lymphocyte Activation Gene-3 Molecule Used as a Vaccine Adjuvant Elicits Greater Humoral and Cellular Immune Responses to Both Particulate and Soluble Antigens", The Journal of Immunology 164:5583-5589 (2000).
Fearson E.R. et al., "Interleukin-2 Production by Tumor Cells Bypasses T Helper Function in the Generation of an Antitumor Response", Cell 60:397-403 (1990).
Finger R.L. et al., "The Human PD-1 Gene: Complete cDNA, Genomic Organization, and Developmentally Regulated Expression in B Cell Progenitors", Gene 197:177-187 (1997).
Fougeray S. et al., "A Soluble LAG-3 Protein as an Immunopotentiator for Therapeutic Vaccines: Preclinical Evaluation of IMP321", Vaccine 24(26):5426-5433 (Jun. 29, 2006).
Wang-Gillam A. et al., "A Phase I Study of IMP321 and Gemcitabine as the Front-line Therapy in Patients with Advanced Pancreatic Adenocarcinoma", Invest New Drugs 31(3):707-713 (2013).
Wang W. et al., "PD1 Blockade Reverses the Suppression of Melanoma Antigen-Specific CTL by CD4+CD25HI Regulatory T Cells", International Immunology 21(9):1065-1077 (2009).
Wang Y. et al., "Evaluation on the antitumor activity of topotecan on fresh human breast cancer cell", Cancer Rearch and Clinic 14(4):225-226 (2002), with English language abstract.
Wherry E.J. et al., "Molecular Signature of CD8+ T Cell Exhaustion During Chronic Viral Infection", Immunity 27:670-684 (Oct. 2007).
Woo S. et al., "Immune Inhibitory Molecules LAG-3 and PD-1 Synergistically Regulate T Cell Function to Promote Tumoral Immune Escape", Cancer Research 72(4):917-927 (Dec. 20, 2011).
Ye B. et al., "T-Cell Exhaustion in Chronic Hepatitis B Infection: Current Knowledge and Clinical Significance", Cell Death and Disease 6:e1694 (2015).
Ye X. et al., "Regulated Delivery of Therapeutic Proteins After In Vivo Somatic Cell Gene Transfer", Science 283:88-91 (1999).
Youngnak P. et al., "Differential Binding Properties of B7-H1 and B7-DC to Programmed Death-1", Biochemical and Biophysical Research Communications 307:672-677 (2003).
Zaidi M.R. et al., "The Two Faces of Interferon-? inCancer", Clin Cancer Res. 17(19):6118-6124 (Oct. 1, 2011).
Zajac A.J. et al., "Viral Immune Evasion Due to Persistence of Activated T Cells Without Effector Function", J. Exp. Med. 188(12):2205-2213 (Dec. 21, 1998).
Zhang Y. et al., "Programmed Death-1 Upregulation is Correlated With Dysfunction of Tumor-Infiltrating CD8+ T Lymphocytes in Human Non-Small Cell Lung Cancer", Cellular & Molecular Immunology 7:389-395 (2010).
Zou W. et al., "Inhibitory B7-Family Molecules in the Tumour Microenvironment", Nature Reviews—Immunology 8:467-477 (Jun. 2008).
NCBI Reference Sequence: NM_005018.2, Gibson A. et al., "*Homo sapiens* Programmed Cell Death 1 (PDCD1), mRNA", J. Immunol. 192(6):2611-2621 (2014).
NCBI Reference Sequence: NM_025239.3, Wang G. et al., "*Homo sapiens* Programmed Cell Death 1 Ligand 2 (PCDD1LG2), mRNA", Xi Bao Yu Fen Zi Mian Yi Zue Za Zhi 29(2):132-136 (2013).
NCBI Reference Sequence: AF233516.1, Freeman G.J. et al., "*Homo sapiens* PD-1 Ligand Precursor, mRNA, Complete CDS", J. Exp. Med. 192(7):1027-1034 (2000).
Safety Study of Anit-LAG-3 With and Without Anti-PD-1 in the Treatment of Solid Tumors, ClinicalTrials.gov, Clinical Trial No. NCT01968109 (4 pages) (2013).
FDA-Guidance for Industry-Estimating the Maximum Safe Starting Dose in Initial Clinical Trials for Therapeutics in Adult Healthy Volunteers, Pharmacology and Toxicology (30 pages) (Jul. 2005).
Principles of Cancer Therapy: The Merck Manual of Diagnosis and Therapy, 18th Edition, p. 1164, table 149-2 (2006).
Highlights of Prescribing Information, Keytruda, Merck & Co., Inc., 12 pages.
Highlights of Prescribing Information, Opdivo, 8 pages.
FDA news release, (2014), FDA approves Keytruda for advanced melanoma, 2 pages.
FDA news release, (2014), FDA approves Opdivo for advanced melanoma, 2 pages.
Environmental Protection Agency, Federal Register, (1992), vol. 57, No. 109, pp. 24152-24173.

(56) References Cited

OTHER PUBLICATIONS

Japanese Office Action dated Nov. 7, 2019 issued in Japanese Patent Application No. 2017-536009, together with an English language translation.
English translation of Japanese Office Action dated Aug. 30, 2018 issued in Japanese Patent Application No. 2016-559686.
Russian Office Action dated Jul. 30, 2019 issued in Russian Patent Application No. 2017127000.
Russian Search Report dated Jul. 29, 2019 issued in Russian Patent Application No. 2017127000.
Russian Office Action dated Feb. 5, 2020 received in Russian Application No. 2017127000, together with an English-language translation.
English translation of Chinese Office Action dated Apr. 28, 2018 issued in Chinese Patent Application No. 201480073584.3.
English translation of Chinese Office Action dated Apr. 28, 2018 issued in CN 20140073584.3.
Great Britain Search Report dated Oct. 22, 2015 received in British Application No. 1500374.2.
Extended European Search Report dated Nov. 13, 2019 issued in European Patent Application No. 19189911.1.
Extended European Search Report dated Mar. 27, 2019 in European Patent Application No. 18 20 8378.2.
International Search Report and Written Opinion dated Mar. 26, 2015 received in International Application No. PCT/EP2014/078779.
International Search Report and Written Opinion dated May 6, 2016 received in International Application No. PCT/EP2016/050321.
United States Office Action dated Feb. 14, 2019 issued in U.S. Appl. No. 15/542,466.
Shapiro M. et al., "Lymphocyte Activation Gene 3: A Novel Therapeutic Target in Chronic Lymphocytic Leukemia", Haematologica 102(5):874-882 (2017).
U.S. Final Office Action dated Aug. 3, 2021 received in U.S. Appl. No. 16/274,466.
Moser K.L. et al., "Genome Scan of Human Systemic Lupus Erythematosus: Evidence for Linkage on Chromosome 1q in African-American Pedigrees", Proc. Natl. Acad. Sci. USA 95:14869-14874 (Dec. 1998).
Nadkarni M.A. et al., "Determination of Bacterial Load by Real-Time PCR Using a Broad-Range (Universal) Probe and Primers Set", Microbiology 148:257-266 (2002).
Nagai E. et al., "Irradiated Tumor Cells Adenovirally Engineered to Secrete Granulocyte/Macrophage-Colony-Stimulating Factor Established Antitumor Immunity and Eliminate Pre-Existing Tumors in Syngeneic Mice", Cancer Immunol Immunother 47:72-80 (1998).
Naidoo J. et al., "Immune Modulation for Cancer Therapy", British Journal of Cancer 111:2214-2219 (2014).
Needleman S.B. et al., "A General Method Applicable to the Search for Similarities in the Amino Acid Sequence of Two Proteins", J. Mol. Biol. 48:443-453 (1970).
Nguyen L.T. et al., "Clinical Blockade of PD1 and LAG3—Potential Mechanisms of Action", Nature Review 13:45-56 (2015).
Nirschl C.J. et al., "Molecular Pathways: Coexpression of Immune Checkpoint Molecules: Signaling Pathways and Implications for Cancer Immunotherapy", Clinical Cancer Research 19(18):4917-4924 (Sep. 15, 2013).
Nowak A.K. et al., "Synergy Between Chemotherapy and Immunotherapy in the Treatment of Established Murine Solid Tumors", Cancer Research 63(15):4490-4496 (Aug. 1, 2003).
Okazaki T. et al., "A Rheostat for Immune Responses: The Unique Properties of PD-1 and Their Advantages for Clinical Application", Nature Immunology 14(12):1212-1218 (Dec. 2013).
Okazaki T. et al., "PD-1 and LAG-3 Inhibitory Co-Receptors Act Synergistically to Prevent Autoimmunity in Mice", JEM, pp. 395-407 (2011).
Pardoll D.M., "The Blockage of Immune Checkpoints in Cancer Immunotherapy", Nature Reviews Cancer 12:252-264 (Apr. 2012).
Parchment R.E., "Bone Marrow as a Critical Normal Tissue that Limits Drug Dose/Exposure in Preclinical Models and the Clinic", In: Tumor Models in Cancer Research, 2nd Edition, Cancer Drug Discovery and Development, Teicher, Ed., pp. 521-552 (2011).
Philips G.K. et al., "Therapeutic Uses of Anti-PD-1 and Anti-PDL1 Antibodies", International Immunology 27(1):39-46 (2014).
Pittet C L et al., "Human Brain Endothelial Cells Endeavor to Immunoregulate CD8 T Cells Via PD-1 Ligand Expression in Multiple Sclerosis", Journal of Neuroinflammation 8:155 (2011).
Plaksin D. et al., "Effective Anti-Metastatic Melonoma Vaccination With Tumor Cells Transfected With Mice Genes and/or Infected With Newcastle Disease Virus (NDV)", Int. J. Cancer 59:796-801 (1994).
Porgador A. et al., "Immunotherapy of Tumor Metastasis Via Gene Therapy", Nat. Immun. 13:113-130 (1994), Abstract.
Postow M.A. et al., "Immune Checkpoint Blockade in Cancer Therapy", Journal of Clinical Oncology 33:1-9 (2015).
Powell C.B. et al., "Reduced Natural Cytotoxic Cell Activity in Patients Receiving Cisplatin-Based Chemotherapy and in Mice Treated with Cisplatin", Clinical Experiments in Immunology 79:424-429 (1990).
Prigent P. et al., "Lymphocyte Activation Gene-3 Induces Tumor Regression and Antitumor Immune Responses", Eur. J. Immunol. 29:3867-3876 (1999).
Rabe H. et al., "*Staphylococcus aureus* Convert Neonatal Conventional CD4+ T Cells into FOXP3+ CD25+ CD127low T Cells Via the PD-1/PD-L1 Axis", Immunology 141:467-481 (2013).
Riott et al., "Antigens are Partially Degraded into Peptides Before Binding to MHC Molecules", Immunology, 4th Edition, pp. 7.9-7.11 (1996).
Rivera V.M. et al., "A Humanized System for Pharmacologic Control of Gene Expression", Nature Med 2(9):1028-1032 (1996).
Robert C. et al., "Anti-Programmed-Death-Receptor-1 Treatment With Pembrolizumab in Ipilimumab-Refractory Advanced Melanoma: a Randomised Dose-Comparison Cohort of a Phase 1 Trial", The Lancet 384:1109-1117 (2014).
Rozali E.N. et al., "Programmed Death Ligand 2 in Cancer-Induced Immune Suppression", Clinical and Development Immunology 2012:656340 (8 pages) (2012).
Rowinsky E.K. et al., "Phase I and Pharmacologic Study of Topotecan: A Novel Topoisomerase I Inhibitor", Journal of Clinical Oncology 10:647-656 (1992).
Salgia R. et al., "Vaccination With Irradiated Autologous Tumor Cells Engineered to Secrete Granulocyte-Macrophage Colony-Stimulating Factor Augments Antitumor Immunity in Some Patients With Metastatic Non-Small Cell Lung Carcinoma", J. Clinical Oncol. pp. 624-630 (2003).
Samulski R J et al., "Helper-Free Stocks of Recombinant Adeno-Associated Viruses: Normal Integration Does Not Require Viral Gene Expression", Journal of Virology 63(9):3822-3828 (Sep. 1989).
Salvadori S. et al., "B7-1 Amplifies the Response to Interleukin-2-Secreting Tumor Vaccines In Vivo, But Fails to Induce a Response by Naïve Cells In Vivo", Human Gene Therapy 6:1299-1306 (1995).
Sawyter T.K. et al., "Src Homology-2 Inhibitors: Peptidomimetic and Nonpeptides", Mini. Rev. in Med. Chem. 2(5):475-488 (2002).
Seung E. et al., "PD-1 Blockade in Chronically HIV-1-Infected Humanized Mice Suppresses Viral Loads", PLOS One8(10):e77780 (Oct. 2013).
Shih K. et al., "Clinical Impact of Checkpoint Inhibitors as Novel Cancer Therapies", Drugs, pp. 1993-2013 (2014).
Shinohara T. et al., "Structure and Chromosomal Localization of the Human PD-1 Gene (PDCD1)", Genomics 23:704-706 (1994).
Simons J.W. et al., "Induction of Immunity to Prostate Cancer Antigens: Results of a Clinical Trial of Vaccination with Irradiated Autologous Prostate Tumor Cells Engineered to Secrete Granulocyte-Macrophage Colony-Stimulating Factor Using Ex Vivo Gene Transfer", Cancer Research 59:5160-5168 (Oct. 15, 1999).
Simons J.W. et al., "Bioactivity of Autologous Irradiated Renal Cell Carcinoma Vaccines Generated by Ex Vivo Granulocyte-Macrophage Colony-Stimulating Factor Gene Transfer", Cancer Research 57:1537-1546 (Apr. 15, 1997).

(56) References Cited

OTHER PUBLICATIONS

Simmons A.D. et al., "GM-CSF-Secreting Cancer Immunotherapies: Preclinical Analysis of the Mechanism of Action", Cancer Immunology, Immunotherapy, Springer, Berlin DE 56:1653-1665 (2007).
Soiffer R. et al., "Vaccination with Irradiated Autologous Melanoma Cells Engineered to Secrete Human Granulocyte-Macrophage Colony-Stimulating Factor Generates Potent Antitumor Immunity in Patients With Metastatic Melanoma", Proc. Natl. Acad. Sci. USA 95:13141-13146 (Oct. 1998).
Suntharalingam G. et al., "Cytokine Storm in a Phase 1 Trial of the Anti-CD28 Monoclonal Antibody TGN1412", The New England Journal of Medicine 355(10):1018-1028 (Sep. 7, 2006).
Swenson L.C. et al., "Comparative Performances of HIV-1 RNA Load Assays at Low Viral Load Levels: Results of an International Collaboration", Journal of Clinical Microbiology 52(2):517-523 (Feb. 2014).
Tafuto S. et al., "A Comparison of Two GM-CSF Schedules to Counteract the Granulo-monocytopenia of Carboplatin-Etoposide Chemotherapy", European Journal of Cancer 31A(1):46-49 (1995).
Tang et al., "The CCL5/CCR5 Axis Promotes Interleukin-6 Production in Human Synovial Fibroblasts", Arthritis & Rheumatism 62(12):3615-3624 (Dec. 2010).
Taylor P.C. et al., "Anti-TNF Biologic Agents: Still the Therapy of Choice for Rheumatoid Arthritis", Nature Reviews Rheumatology 5:578-582 (Oct. 2009).
Teng M.N. et al., "Long-Term Inhibition of Tumor Growth by Tumor Necrosis Factor in the Absence of Cachexia or T-cell Immunity", PNAS 88:3535-3539 (1991).
Togno-Peirce C. et al., "Sex-Associated Expression of Co-Stimulatory Molecules CD80, CD86, and Accessory Molecules, PDL-1, PDL-2 and MHC-II, in F480+ Macrophages During Murine Cysticercosis", BioMed Research International 2013:570158 (9 pages) (2013).
Triebel F., "LAG-3: A Regulator of T-Cell and DC Responses and its Use in Therapeutic Vaccination", Trends in Immunology 24(12):619-622 (Dec. 2003).
Triebel F. et al., "Lag-3, A Novel Lymphocyte Activation Gene Closely Related to CD4", J. Exp. Med. 171:1393-1405 (1990).
Tseng S-Y et al., "B7-DC, a New Dendritic Cell Molecule With Potent Costimulatory Properties for T Cells", J. Exp. Med. 193(7):839-845 (Apr. 2, 2001).
Tsushima F. et al., "Preferential Contribution of B7-H1 to Programmed Death-1-Medated Regulation of Hapten-Specific Allergic Inflammatory Responses", Eur. J. Immunol. 33:2773-2782 (2003).
Velu V. et al., "Role of PD-1 Co-Inhibitory Pathway in HIV Infection and Potential Therapeutic Options", Retrovirology 12(14);17 pages (2015).
Vibhaker R. et al., "Activation-Induced Expression of Human Programmed Death-1 Gene in T-Lymphocytes", Experimental Cell Research 232:25-28 (1997).
Walczak J.R. et al., "Pharmacological Treatments for Prostate Cancer", Expert Opin. Investig. Drugs. 11:1737-1748 (2002), Abstract.
Frank H. et al., "The Determination of Plasma vol. in Man with Radioactive Chromic Chloride", From the Biophysical Laboratory and the Department of Medicine, Harvard Medical School, and the Medical Clinic, Peter Bent Brigham Hospital, Boston, Mass., pp. 991-999 (1953).
Gallimore A. et al., "Induction and Exhaustion of Lymphocytic Choriomeningitis Virus-Specific Cytotoxic T Lymphocytes Visualized Using Soluble Tetrameric Major Histocompatibility Complex Class I-Peptide Complexes", J. Exp. Med. 187(9):1383-1393 (May 4, 1998).
Gansbacher B. et al., "Retroviral Vector-Mediated y-Interferon Gene Transfer into Tumor Cells Generates Potent and Long Lasting Antitumor Immunity", Cancer Research 50:7820-7825 (Dec. 15, 1990).
Gansbacher B. et al., "Interleukin 2 Gene Transfer into Tumor Cells Abrogates Tumorigenicity and Induces Protective Immunity", J. Exp. Med. 172:1217-1224 (Oct. 1990).

Ghiotto M. et al., "PD-L1 and PD-L2 Differ in Their Molecular Mechanisms of Interaction With PD-1", Int Immunol 22(8):651-660 (Aug. 2010).
Goding S.R. et al., "Restoring Immune Function of Tumor-Specific CD4+ T Cells During Recurrence of Melanoma", The Journal of Immunology 10:4899-4909 (2013).
Goldschmidt P.L. et al, "Comparison of an Amplified Enzyme-Linked Immunosorbent Assay With Procedures Based on Molecular Biology for Assessing Human Immunodeficiency Virus Type 1 Viral Load", Clinical and Diagnostic Laboratory Immunology 5(4):513-518 (Jul. 1998).
Goldsmith M.A. et al., "Quantitative Prediction of Drug Toxicity in Humans from Toxicology in Small and Large Animals", Cancer Research 35:1354-1364 (1975).
Golumbeck P.T. et al., "Treatment of Established Renal Cancer by Tumor Cells Engineered to Secrete Interleukin-4", Science 254:713-716 (1991).
Griswold, Jr. D.P., "Consideration of the Subcutaneously Implanted B16 Melanoma as a Screening Model for Potential Anticancer Agents", Cancer Chemotherapy Reports Part 2, 3(1):315-324 (Nov. 1972).
Guo Z S et al., "Evaluation of Promoter Strength for Hepatic Gene Expression In Vivo Following Adenovirus-Mediated Gene Transfer", Gene Therapy 3(9):802-810 (1996).
Harvey RD, "Immunologic and Clinical Effects of Targeting PD-1 in Lung Cancer", Clinical Pharmacology & Therapeutics 96(2):214-223 (Aug. 2014).
Hatam L.J. et al., "Immune Suppression in Premalignant Respiratory Papillomas: Enriched CD4+Foxp3 + Regulatory T Cells and PD-1/PD-L1/L2 Expression", Clinical Cancer Research 18(7):1925-1935 (2012).
Havell E.A. et al., "The Antitumor Function of Tumor Necrosis Factor (TNF)", J. Exp. Med. 167(3):1067-1085 (Mar. 1988).
He J. et al., "Circulating Precursor CCR7IoPD-1hi CXCR5+ CD4+ T Cells Indicate The Cell Activity and Promote Antibody Responses Upon Antigen Reexposure", Immunity 39:770-781 (Oct. 17, 2013).
Hock H. et al., "Interleukin 7 Induces CD4+ T Cell-dependent Tumor Rejection", J Exp Med 174:1291-1298 (1991).
Hofmeyer K.A. et al., "The PD-1/PD-L1 (B7-H1) Pathway in Chronic Infection-Induced Cytotoxic T Lymphocyte Exhaustion", Journal of Biomedicine and Biotechnology vol. 2011, Article ID 451694 (2011).
Holguín A. et al., "Comparison of Three Different Commercial Methods for Measuring Plasma Viraemia in Patients Infected with Non-B HIV-1 Subtypes", Eur J Clin Microbiol Infect Dis 18:256-259 (1999).
Hom S.S. et al., "Common Expression of Malenoma Tumor-Associated Antigens Recongnized by Human Tumor Infiltrating Lymphocytes: Analysis by Human Lymphocyte Antigen Restriction", Journal of Immunotherapy, 10:153-164 (1991).
Honeyborne I. et al., "The Molecular Bacterial Load Assay Replaces Solid Culture for Measuring Early Bactericidal Response to Anti-tuberculosis Treatment", Journal of Clinical Microbiology 52(8):3064-3067 (Aug. 2014).
Honeyborne I. et al., "Molecular Bacterial Load Assay, a Culture-Free Biomarker for Rapid and Accurate Quantification of Sputum *Mycobacterium tuberculosis* Bacillary Load during Treatment", Journal of Clinical Microbiology, 49(11):3905-3911 (Nov. 2011).
Hu H-M et al., "Development of Antitumor Immune Responses in Reconstituted Lymphopenic Hosts", Advances in Brief 62:3914-3919 (Jul. 15, 2002).
Huang A.Y.C. et al., "Role of Bone Marrow-Derived Cells in Presenting MHC Class I-Restricted Tumor Antigens", Science 264:961-965 (1994).
Huard B. et al., "Characterization of the Major Histocompatibility Complex Class II Binding Site on LAG-3 Protein", Proc. Natl. Acad. Sci. USA 94:5744-5749 (May 1997).
Huebner K. et al., "The Human Gene Encoding GM-CSF is at 5q21-q32, the Chromosome Region Deleted in the 5q-Anomaly", Science 230(4731):1282-1285 (1985).
Ill C.R. et al., "Optimization of the Human Factor VIII Complementary DNA Expression Plasmid for Gene Therapy of Hemophilia A", Blood Coagul Fibrinolysis 8 Suppl. 2:S23-S30 (1997), Abstract.

(56) References Cited

OTHER PUBLICATIONS

Ishida Y. et al., "Induced Expression of PD-1, a Novel Member of the Immunoglobulin Gene Superfamily, Upon Programmed Cell Death", The EMBO Journal 11(11):3887-3895 (1992).
Jaffee EM et al., "Gene Therapy: Its Potential Application in the Treatment of Renal-Cell Carcinoma", Seminars in Oncology 22:81-91 (1995).
Jaffee EM et al., "Novel Allogeneic Granulocyte-Macrophage Colony-Stimulating Factor-Secreting Tumor Vaccine for Pancreatic Cancer: A Phase I Trial of Safety and Immune Activation", Journal of Clinical Oncology 19(1):145-156 (2001), Abstract.
Karim R. et al., "Tumor-Expressed B7-H1 and B7-DC in Relation to PD-1+ T-Cell Infiltration and Survival of Patients With Cervical Carcinoma", Clin Cancer Res 15(20):6341-6347 (Oct. 15, 2009).
Kawakami Y. et al., "Shared Human Melanoma Antigens, Recognition by Tumor-Infiltrating Lymphocytes in HLA-A2. 1-Transfected Melanomas", J. Immunol. 148:638-643 (1992), (Abstract).
Kelly K. et al., "Avelumab (MSB0010718C), an Anti-PD-L1 Antibody, in Patients With Metastatic or Locally Advanced Solid Tumors: Assessment of Safety and Tolerability in a Phase I, Open-Label Expansion Study", J Clin Oncol vol. 33 ASC University (4 pages) (2015).
Kirkin A.F. et al., "Melanoma-Associated Antigens Recognized by Cytotoxic T Lymphocytes", APMIS 106:665-679 (1998).
Kim D.W. et al., "Use of Human Elongation Factor 1? Promoter as a Versatile and Efficient Expression System", Gene 91(2):217-223 (1990).
Klein E.K. et al., "Properties of the K562 Cell Line, Derived from a Patient with Chronic Myeloid Leukemia", Int. J. Cancer 18:421-431 (1976).
Koh T.J. et al., "Inflammation and Wound Healing: The Role of the Macrophage", Expert Rev Mol Med 13(e23): 14 pages (2013).
Kruskal J.B., "An Overview of Sequence Comparison", Chapter 1, pp. 1-44 (1983).
Larkin M.A. et al., "Clustal W and Clustal X Version 2.0", Bioinformatics 23 (21):2947-2948 (2007).
Latchman Y. et al., "PD-L2 is a Second Ligand for PD-1 and Inhibits T Cell Activation", Nature Immunology 2(3):261-268 (Mar. 2001).
Lee C-T et al., "Genetic Immunotherapy of Established Tumors with Adenovirus-Murine Granulocyte-Macrophage Colony-Stimulating Factor", Human Gene Therapy 8:187-193 (1997).
Lee K-H et al., "Increased Vaccine-Specific T Cell Frequency After Peptide-Based Vaccination Correlates With Increased Susceptibility to In Vitro Stimulation But Does Not Lead to Tumor Regression", The Journal of Immunology 163:6292-6300 (1999).
Leveque D. et al., "Pharmacokinetics of Therapeutic Monoclonal Antibodies Used in Oncology", Anticancer Resarch 25:2327-2344 (2005).
Li B. et al., "Lymphocyte Activation Gene-3 Fusion Protein Increases the Potency of a Granulocyte Macrophage Colony-Stimulating Factor-Secreting Tumor Cell Immunotherapy", Clinical Cancer Research 14(11):3545-3554 (Jun. 1, 2008).
Li B. et al., "Recombinant IL-7 Enhances the Potency of GM-CSF-Screening Tumor Cell Immunotherapy", Clinical Immunology Academic Press, US 123:155-165 (2007).
Li B. et al., "Established B16 Tumors are Rejected Following Treatment with GM-CSF-Secreting Tumor Cell Immunotherapy in Combination With Anti-4 1BB mAB", Clinical Immunology Academic Press, U.S. 125:76-87 (2007).
Lozzio C.B. et al., "Human Chronic Myelogenous Leukemia Cell-Line with Positive Philadelphia Chromosome", Blood 45(3)321-334 (1975).
Matsuzaki J. et al., "Tumor-Infiltrating NY-ESO-1-Specific CD8+ T Cells are Negatively Regulated by LAG-3 and PD-1 in Human Ovarian Cancer", PNAS 107(17):7875-7880 (Apr. 27, 2010).

Maxwell M.B. et al., "Chemotherapy-Induced Myelosuppression", Seminars in Oncology Nursing vol. 8 (2):113-123 (1992).
Menzies A.M. et al., "New Combinations and Immunotherapies for Melanoma", Ther Adv Med Oncol. 5(5):278-285 (2013).
Miller M.D. K.M. et al., "Paclitaxel Plus Bevacizumab Versus Paclitaxel Alone for Metastatic Breast Cancer", The New England Journal of Medicine 357:2666-2676 (Dec. 27, 2007).
Clinical Trial Study NCT00351949 (version 2) (2006).
U.S. non-Final Office Action dated Apr. 20, 2022 received in related U.S. Appl. No. 16/274,466.
Clinical Trail Study NCT00349934 (version 1), IMP321 Phase 1 Breast Carcinoma, first posted on Jul. 10, 2006.
U.S. non-Final Office Action dated Feb. 19, 2021 received in U.S. Appl. No. 16/274,466.
Andreae S. et al., "Maturation and Activation of Dendritic Cells Induced by Lymphocyte Activation Gene-3 (CD223)", The Journal of Immunology 168:3874-3880 (2002).
Hemon P. et al., "MHC Class II Engagement by its Ligand LAG-3 (CD223) Contributes to Melanoma Resistance to Apoptosis", The Journal of Immunology 186(9):5173-5183 (May 1, 2011).
Kholodov L.E. et al., "Clinical Pharmacokinetics", M.: Medicine., pp. 83-98, 134-138, 160, 378-380 (1985) (cited and discussed in the Office Action (English translation provided) dated Dec. 27, 2021 issued in Russian Application No. 2017127000/04(046505)).
Kondo M. et al., "Early Monocytopenia After Chemotheray as a Risk Factor for Neutropenia", American Journal of Clinical Oncology 22(1):103-105 (Feb. 1999).
Legat A. et al., "Vaccination With LAG-3IG (IMP321) and Peptides Induces Specific CD4 and CD8 T-Cell Responses in Metastatic Melanoma Patients-Report of a Phase I/IIa Clinical Trial", Clinical Cancer Research 22(6):1330-1340 (Mar. 15, 2016).
Sergeev M. et al., "A short Course in Molecular Pharmacology", M.: Moscow Medical Institute named after N.I. Pirogov, p. 10 (1975) (cited and discussed in the Office Action (English translation provided) dated Dec. 27, 2021 issued in Russian Application No. 2017127000/04(046505)).
Russian Office Action dated Dec. 27, 2021 received in Russian Application No. 2017127000/04(046505), together with an English-language translation.
Loken M.R. et al., "Establishing Optimal Lymphocyte Gates for Immunophenotyping by Flow Cytometry", Cytometry 11(4):453-469 (1990) (cited in CN OA dated Apr. 28, 2023).
Nicholson J.K.A. et al., "Use of CD45 Fluorescence and Side-Scatter Characteristics for Gating Lymphocytes When Using the Whole Blood Lysis Procedure and Flow Cytometry", Cytometry (Communications in Clinical Cytometry) 26:16-21 (1996) (cited in CN OA dated Apr. 28, 2023).
Chinese Office Action dated Apr. 28, 2023 received in Chinese Application No. 202111358413.3, together with an English-language translation.
Chinese Office Action dated Aug. 31, 2023 received in Chinese Application No. 202111344452.8, together with an English-language translation.
Desoize B. et al., "Particular Aspects of Platinum Compounds Used at Present in Cancer Treatment", Critical Reviews in Oncology/Hematology 42:317-325 (Dec. 31, 2002).
Hao Y., "Study on the Regular, Long-Circulating and Temperature-Sensitive Liposomes of Topotecan Hydrochloride", Chinese Doctoral Dissertations Full-text Database, Medicine and Health Sciences, No. 3 (Mar. 15, 2011), cited in Chinese Office Action dated Jul. 30, 2024 received in Chinese Application No. 202110293412.9.
Chinese Office Action & Search Report dated Jul. 30, 2024 received in Chinese Application No. 202110293412.9, together with an English-language translation.

\* cited by examiner

```
          10         20         30         40         50         60
    LQPGAEVPVV WAQEGAPAQL PCSPTIPLQD LSLLRRAGVT WQHQPDSGPP AAAPGHPLAP 70         80         90        100        110        120
    GPHPAAPSSW GPRPRRYTVL SVGPGGLRSG RLPLQPRVQL DERGRQRGDF SLWLRPARRA 130        140        150        160        170        180
    DAGEYRAAVH LRDRALSCRL RLRLGQASMT ASPPGSLRAS DWVILNCSFS RPDRPASVHW 190        200        210        220        230        240
    FRNRGQGRVP VRESPHHHLA ESFLFLPQVS PMDSGPWGCI LTYRDGFNVS IMYNLTVLGL 250        260        270        280        290        300
    EPPTPLTVYA GAGSRVGLPC RLPAGVGTRS FLTAKWTPPG GGPDLLVTGD NGDFTLRLED 310        320        330        340        350        360
    VSQAQAGTYT CHIHLQEQQL NATVTLAIIT VTPKSFGSPG SLGKLLCEVT PVSGQERFVW 370        380        390        400        410        420
    SSLDTPSQRS FSGPWLEAQE AQLLSQPWQC QLYQGERLLG AAVYFTELSS PGAQRSGRAP 430        440        450        460        470        480
    GALPAGHLLL FLTLGVLSLL LLVTGAFGFH LWRRQWRPRR FSALEQGIHP QAQSKIEELE 490        500
    QEPEPEPEPE PEPEPEPEPE QL
```

COMBINED PREPARATIONS FOR THE TREATMENT OF CANCER

CROSS REFERENCE TO RELATED APPLICATIONS

This application is a continuation of U.S. application Ser. No. 15/105,789, filed Jun. 17, 2016, which is a National Stage Entry of International Application No. PCT/EP2014/078779, filed Dec. 19, 2014, which claims priority from GB 1322626.1, filed on Dec. 19, 2013, the entire contents of which are incorporated herein by reference herein.

This invention relates to combined preparations and to pharmaceutical compositions, and their use as medicaments, in particular for the treatment of cancer, and to methods for the treatment of cancer.

Cancer may be treated with one or more cytotoxic anti-neoplastic drugs ("chemotherapeutic agents") as part of a standardized regimen. Chemotherapy may be aimed at curing a patient, or at prolonging life, or alleviating symptoms.

Conventional chemotherapeutic agents act by killing cells that divide rapidly, exploiting one of the properties of most cancer cells. However, chemotherapy also harms cells that divide rapidly under normal circumstances, for example cells in the bone marrow, digestive tract, and hair follicles. This causes the most common side-effects of chemotherapy: myelosuppression (decreased production of blood cells, hence also immunosuppression), mucositis (inflammation of the lining of the digestive tract), and alopecia (hair loss).

There is a need to provide more effective cancer treatments, and to provide effective cancer treatments with reduced side effects.

The lymphocyte activation gene 3 (LAG-3) is a CD4 homolog type I membrane protein with four extracellular Ig superfamily domains. Similar to CD4, LAG-3 oligomerizes at the surfaces of T cells and binds to MHC class II molecules on antigen-presenting cells (APCs) but with significantly higher affinity than CD4. LAG-3 is expressed on activated CD4-positive and CD8-positive T lymphocytes where it associates with the CD3-TCR complex at the cell surface and negatively regulates signal transduction. As a consequence, it negatively regulates T cell proliferation, function, and homeostasis.

LAG-3-derived soluble fusion proteins, have been shown to bind MHC class II molecules with a much higher avidity than CD4, to increase the capacity of MHC class II-positive macrophages and immature dendritic cells to induce T cell responses in vitro, and to enhance the in vitro induction of viral and tumor-specific cytotoxic T cells. Accordingly, a LAG-3 fusion protein is used as a systemic immunostimulant and as an adjuvant for cancer vaccines.

WO 2009/044273 describes use of recombinant LAG-3 protein, or derivatives thereof, for boosting a monocyte-mediated immune response, in particular to induce an increase in the number of monocytes in blood, for the treatment of cancer.

It has now surprisingly been found that administration of LAG-3 protein, or a derivative thereof that is able to bind to MHC class II molecules, and a platinum-based anti-neoplastic agent, or a topoisomerase I inhibitor, has a synergistic effect on reducing tumor growth.

According to the invention there is provided a combined preparation, which comprises: (a) LAG-3 protein, or a derivative thereof that is able to bind to MHC class II molecules; and (b) an anti-neoplastic agent, wherein the anti-neoplastic agent is a platinum-based anti-neoplastic agent or a topoisomerase I inhibitor.

The term "combined preparation" as used herein refers to a "kit of parts" in the sense that the combination components (a) and (b) as defined above can be dosed independently or by use of different fixed combinations with distinguished amounts of the combination components (a) and (b). The components can be administered simultaneously or one after the other. If the components are administered one after the other, preferably the time interval between administration is chosen such that the therapeutic effect of the combined use of the components is greater than the effect which would be obtained by use of only any one of the combination components (a) and (b).

The components of the combined preparation may be present in one combined unit dosage form, or as a first unit dosage form of component (a) and a separate, second unit dosage form of component (b). The ratio of the total amounts of the combination component (a) to the combination component (b) to be administered in the combined preparation can be varied, for example in order to cope with the needs of a patient sub-population to be treated, or the needs of the single patient, which can be due, for example, to the particular disease, age, sex, or body weight of the patient.

Preferably, there is at least one beneficial effect, for example an enhancing of the effect of the anti-neoplastic agent, or a mutual enhancing of the effect of the combination components (a) and (b), for example a more than additive effect, additional advantageous effects, fewer side effects, less toxicity, or a combined therapeutic effect compared with an effective dosage of one or both of the combination components (a) and (b), and very preferably a synergism of the combination components (a) and (b).

A combined preparation of the invention may be provided as a pharmaceutical combined preparation for administration to a mammal, preferably a human. The LAG-3 protein, or derivative thereof, may optionally be provided together with a pharmaceutically acceptable carrier, excipient, or diluent, and/or the anti-neoplastic agent may optionally be provided together with a pharmaceutically acceptable carrier, excipient, or diluent.

The LAG-3, or derivative thereof, may be present at a dose which is a molar equivalent of 0.25-30 mg, 1-30 mg, or 6-30 mg of the LAG-3 derivative LAG-3Ig fusion protein IMP321. Doses of 6-30 mg per subcutaneous (s.c.) injection of IMP321 have been shown to be safe and provide an acceptable systemic exposure based on the results of pharmacokinetics data obtained in metastatic renal cell cancer patients. A blood concentration of IMP321 superior to 1 ng/ml for at least 24 hours after s.c. injection is obtained in patients injected with IMP321 doses of more than 6 mg.

A combined preparation of the invention may comprise a plurality of doses of the LAG-3 protein, or derivative thereof.

The dose of the anti-neoplastic agent will depend on the particular anti-neoplastic agent being used.

Platinum-based anti-neoplastic agents are coordination complexes of platinum used in cancer chemotherapy. They are believed to form cross-links in DNA that inhibit DNA repair and/or DNA synthesis resulting in cell death. The main dose-limiting side effect of cancer treatment using platinum compounds is peripheral neurotoxicity. Examples of platinum-based anti-neoplastic agents include cisplatin, carboplatin, oxaliplatin, satraplatin, picoplatin, Nedaplatin, and Triplatin.

Carboplatin, or cis-diammine(cyclobutane-1,1-dicarboxylate-O,O')platinum(I) (trade names Paraplatin and Paraplatin-AQ), is used against some forms of cancer (mainly ovarian carcinoma, lung, head and neck cancers as well as endometrial, esophageal, bladder, breast and cervical; central nervous system or germ cell tumors; osteogenic sarcoma, and as preparation for a stem cell or bone marrow transplant). It has greatly reduced side-effects compared to its parent compound cisplatin. Guidelines for carboplatin dosing are available from the US Food and Drug Administration (FDA).

Oxaliplatin, or [(1R,2R)-cyclohexane-1,2-diamine](ethanedioato-O,O')platinum(II) (trade name Eloxatin), comprises a square planar platinum(II) centre. In contrast to cisplatin and carboplatin, oxaliplatin comprises the bidentate ligand 1,2-diaminocyclohexane in place of the two monodentate amine ligands. It also has a bidentate oxalate group. Oxaliplatin has anti-tumor activity against colon carcinoma. Oxaliplatin functions by forming both inter- and intra-strand cross links in DNA. Cross links in DNA prevent DNA replication and transcription, resulting in cell death. The recommended dose of oxaliplatin in an adjuvant setting is 85 mg/m$^2$ intravenously repeated every two weeks for 12 cycles. A recommended dose for oxaliplatin in treatment of metastatic colorectal cancer is 85 mg/m$^2$ intravenously repeated every two weeks until disease progression or unacceptable toxicity.

Topoisomerase inhibitors are agents designed to interfere with the action of topoisomerase enzymes (topoisomerase I and II), which are enzymes that control changes in DNA structure by catalyzing the breaking and rejoining of the phosphodiester backbone of DNA strands during the normal cell cycle. It is thought that topoisomerase inhibitors block the ligation step of the cell cycle, generating single and double stranded breaks that harm the integrity of the genome. Introduction of these breaks subsequently leads to apoptosis and cell death.

Human DNA topoisomerase I (Top1) is an essential enzyme that relaxes DNA supercoiling during replication and transcription. Top1 generates DNA single-strand breaks that allow rotation of the cleaved strand around the double helix axis. Top1 also re-ligates the cleaved strand to re-establish intact duplex DNA. Top1-DNA intermediates, known as cleavage complexes, are transient and present at low levels under normal circumstances. However, treatment with Top1 inhibitors, such as the camptothecins, stabilizes the cleavable complexes, prevents DNA religation and induces lethal DNA strand breaks. Cancer cells are selectively sensitive to the generation of these DNA lesions.

Topotecan, or (S)-10-[(dimethylamino)methyl]-4-ethyl-4,9-dihydroxy-1H-pyrano[3',4':6,7]indolizino[1,2-b] quinoline-3,14(4H,12H)-dione monohydrochloride (trade name Hycamtin), is a chemotherapeutic agent that is a topoisomerase I inhibitor. It is a water-soluble derivative of camptothecin. It is used in form of the hydrochloride to treat ovarian cancer and lung cancer, as well as other cancer types. Topotecan is a semi-synthetic derivative of camptothecin. Camptothecin is a natural product extracted from the bark of the tree *Camptotheca acuminata*. Topoisomerase-I is a nuclear enzyme that relieves torsional strain in DNA by opening single strand breaks. Once topoisomerase-I creates a single strand break, the DNA can rotate in front of the advancing replication fork. Topotecan intercalates between DNA bases. This intercalation disrupts the DNA duplication machinery when it reaches a site where topotecan is intercalated. This disruption prevents DNA replication, and ultimately leads to cell death. Mammalian cells cannot efficiently repair these double strand breaks. This process leads to breaks in the DNA strand resulting in apoptosis.

A recommended dose of Hycamtin capsules is 2.3 mg/m$^2$ body surface area/day administered for five consecutive days with a three week interval between the start of each course.

Another camptothecin derivative irinotecan (CPT11) is approved for the treatment of colon cancer.

A combined preparation of the invention may comprise a plurality of doses of the anti-neoplastic agent.

The LAG-3 protein may be an isolated natural or recombinant LAG-3 protein. The LAG-3 protein may comprise an amino sequence of LAG-3 protein from any suitable species, such as a primate or murine LAG-3 protein, but preferably a human LAG-3 protein. The amino acid sequence of human and murine LAG-3 protein is provided in FIG. 1 of Huard et al (*Proc. Natl. Acad. Sci. USA*, 11: 5744-5749, 1997). The sequence of human LAG-3 protein is repeated in FIG. 13 below (SEQ ID NO: 1). The amino acid sequences of the four extracellular Ig superfamily domains (D1, D2, D3, and D4) of human LAG-3 are also identified in FIG. 1 of Huard et al., at amino acid residues: 1-149 (D1); 150-239 (D2); 240-330 (D3); and 331-412 (D4).

Derivatives of LAG-3 protein include fragments, variants, or mutants of LAG-3 protein that are able to bind MHC class II molecules. Several derivatives of LAG-3 protein are known that are able to bind to MHC class II molecules. Many examples of such derivatives are described in Huard et al (*Proc. Natl. Acad. Sci. USA*, 11: 5744-5749, 1997). This document describes characterization of the MHC class II binding site on LAG-3 protein. Methods for making mutants of LAG-3 are described, as well as a quantitative cellular adhesion assay for determining the ability of LAG-3 mutants to bind class II-positive Daudi cells. Binding of several different mutants of LAG-3 to MHC class II molecules was determined. Some mutations were able to reduce class II binding, while other mutations increased the affinity of LAG-3 for class II molecules. Many of the residues essential for binding MHC class II proteins are clustered at the base of a large 30 amino acid extra-loop structure in the LAG-3 D1 domain. The amino acid sequence of the extra-loop structure of the D1 domain of human LAG-3 protein is GPPAAAPGHPLAPGPHPAAPSSWGPRPRRY (SEQ ID NO: 2), the underlined sequence in FIG. 13.

The LAG-3 protein derivative may comprise the 30 amino acid extra-loop sequence of the human LAG-3 D1 domain, or a variant of such sequence with one or more conservative amino acid substitutions. The variant may comprise amino acid sequence that has at least 70%, 80%, 90%, or 95% amino acid identity with the 30 amino acid extra-loop sequence of the human LAG-3 D1 domain.

The derivative of LAG-3 protein may comprise an amino acid sequence of domain D1, and optionally domain D2, of LAG-3 protein, preferably human LAG-3 protein.

The derivative of LAG-3 protein may comprise an amino acid sequence that has at least 70%, 80%, 90%, or 95% amino acid identity with domain D1, or with domain D1 and D2, of LAG-3 protein, preferably human LAG-3 protein.

The derivative of LAG-3 protein may comprise an amino acid sequence of domains D1, D2, D3, and optionally D4, of LAG-3 protein, preferably human LAG-3 protein.

The derivative of LAG-3 protein may comprise an amino acid sequence that has at least 70%, 80%, 90%, or 95% amino acid identity with domain D1, D2, and D3, or with domain D1, D2, D3, and D4, of LAG-3 protein, preferably human LAG-3.

Sequence identity between amino acid sequences can be determined by comparing an alignment of the sequences.

When an equivalent position in the compared sequences is occupied by the same amino acid, then the molecules are identical at that position.

Scoring an alignment as a percentage of identity is a function of the number of identical amino acids at positions shared by the compared sequences. When comparing sequences, optimal alignments may require gaps to be introduced into one or more of the sequences to take into consideration possible insertions and deletions in the sequences. Sequence comparison methods may employ gap penalties so that, for the same number of identical molecules in sequences being compared, a sequence alignment with as few gaps as possible, reflecting higher relatedness between the two compared sequences, will achieve a higher score than one with many gaps. Calculation of maximum percent identity involves the production of an optimal alignment, taking into consideration gap penalties.

Suitable computer programs for carrying out sequence comparisons are widely available in the commercial and public sector. Examples include MatGat (Campanella et al., 2003, BMC Bioinformatics 4: 29; program available from http://bitincka.com/ledion/matgat), Gap (Needleman & Wunsch, 1970, J. Mol. Biol. 48: 443-453), FASTA (Altschul et al., 1990, J. Mol. Biol. 215: 403-410; program available from http://www.ebi.ac.uk/fasta), Clustal W 2.0 and X 2.0 (Larkin et al., 2007, Bioinformatics 23: 2947-2948; program available from http://www.ebi.ac.uk/tools/clustalw2) and EMBOSS Pairwise Alignment Algorithms (Needleman & Wunsch, 1970, supra; Kruskal, 1983, In: Time warps, string edits and macromolecules: the theory and practice of sequence comparison, Sankoff & Kruskal (eds), pp 1-44, Addison Wesley: programs available from http://www.ebi-.ac.uk/tools/emboss/align). All programs may be run using default parameters.

For example, sequence comparisons may be undertaken using the "needle" method of the EMBOSS Pairwise Alignment Algorithms, which determines an optimum alignment (including gaps) of two sequences when considered over their entire length and provides a percentage identity score. Default parameters for amino acid sequence comparisons ("Protein Molecule" option) may be Gap Extend penalty: 0.5, Gap Open penalty: 10.0, Matrix: Blosum 62.

The sequence comparison may be performed over the full length of the reference sequence.

The LAG-3 protein derivative may be fused to Immunoglobulin Fc amino acid sequence, preferably human IgG1 Fc amino acid sequence, optionally by a linker amino acid sequence.

The ability of a derivative of LAG-3 protein to bind to MHC class II molecules may be determined using a quantitative cellular adhesion assay as described in Huard et al (supra). The affinity of a derivative of LAG-3 protein for MHC class II molecules may be at least 20%, 30%, 40%, 50%, 60%, 70%, 80%, 90%, or 100% of the affinity of human LAG-3 protein for class II molecules. Preferably the affinity of a derivative of LAG-3 protein for MHC class II molecules is at least 50% of the affinity of human LAG-3 protein for class II molecules.

Examples of suitable derivatives of LAG-3 protein that are able to bind MHC class II molecules include derivatives comprising:
- amino acid residues 23 to 448 of the human LAG-3 sequence;
- amino acid sequence of domains D1 and D2 of LAG-3;
- amino acid sequence of domains D1 and D2 of LAG-3 with an amino acid substitution at one or more of the following positions: position 73 where ARG is substituted with GLU; position 75 where ARG is substituted with ALA or GLU; position 76 where ARG is substituted with GLU; position 30 where ASP is substituted with ALA; position 56 where HIS is substituted with ALA: position 77 where TYR is substituted with PHE; position 88 where ARG is substituted with ALA; position 103 where ARG is substituted with ALA; position 109 where ASP is substituted with GLU; position 115 where ARG is substituted with ALA;
- amino acid sequence of domain D1 of LAG-3 with a deletion of amino acid residues 54 to 66;
- a recombinant soluble human LAG-3Ig fusion protein (IMP321)—a 200-kDa dimer produced in Chinese hamster ovary cells transfected with a plasmid encoding for the extracellular domain of hLAG-3 fused to the human IgG1 Fc.

According to the invention there is also provided a pharmaceutical composition, which comprises (a) LAG-3 protein, or a derivative thereof that is able to bind to MHC class II molecules; (b) an anti-neoplastic agent, wherein the anti-neoplastic agent is a platinum-based anti-neoplastic agent or a topoisomerase I inhibitor; and (c) a pharmaceutically acceptable carrier, excipient, or diluent.

According to the invention there is further provided a combined preparation, or pharmaceutical composition, of the invention for use as a medicament.

The invention also provides a combined preparation, or pharmaceutical composition, of the invention for preventing, treating, or ameliorating cancer.

There is further provided according to the invention use of a combined preparation, or pharmaceutical composition, of the invention in the manufacture of a medicament for preventing, treating, or ameliorating cancer.

There is also provided according to the invention a method of preventing, treating, or ameliorating cancer, which comprises administering LAG-3 protein, or a derivative thereof that is able to bind to MHC class II molecules, and an anti-neoplastic agent, to a subject in need of such prevention, treatment, or amelioration, wherein the anti-neoplastic agent is a platinum-based anti-neoplastic agent or a topoisomerase 1 inhibitor.

The LAG-3 protein, or derivative thereof, and the anti-neoplastic agent may be administered sequentially to the subject, i.e. the LAG-3 protein, or derivative thereof, may be administered before, with, or after the anti-neoplastic agent.

The LAG-3 protein, or derivative thereof, and the anti-neoplastic agent may be administered to the subject within 96 hours, 72 hours, 48 hours, 24 hours, or 12 hours, of each other.

Alternatively, the LAG-3 protein, or derivative thereof, and the anti-neoplastic agent may be co-administered to the subject, for example as a composition comprising the LAG-3 protein, or derivative thereof, and the anti-neoplastic agent, or by simultaneous administration of separate doses of the LAG-3 protein, or derivative thereof, and the anti-neoplastic agent.

According to some embodiments, a plurality of doses of the LAG-3 protein, or derivative thereof, and/or a plurality of doses of the anti-neoplastic agent, is administered to the subject.

According to some embodiments, a dose of the LAG-3 protein, or derivative thereof, is administered before, with, or after each administration of two or more doses of the anti-neoplastic agent.

For example, a dose of the LAG-3 protein, or derivative thereof, may be administered within 96 hours, 72 hours, 48 hours, 24 hours, or 12 hours, of each administration of two or more doses of the anti-neoplastic agent.

The choice of appropriate dosages of the components used in combination therapy according to the present invention can be determined and optimized by the skilled person, for example, by observation of the patient, including the patient's overall health, and the response to the combination therapy. Optimization, for example, may be necessary if it is determined that a patient is not exhibiting the desired therapeutic effect or conversely, if the patient is experiencing undesirable or adverse side effects that are too many in number or are of a troublesome severity.

The doses of the components used in combination therapy according to the invention should be chosen to provide a therapeutically effective amount of the components in combination. An "effective amount" of the combination therapy is an amount that results in a reduction of at least one pathological parameter associated with cancer. For example, in some embodiments, an effective amount of the combination therapy is an amount that is effective to achieve a reduction of at least about 10%, 20%, 30%, 40%, 50%, 60%, 70%, 80%, or 90%, in the parameter, compared to the expected reduction in the parameter associated with the cancer without the combination therapy. For example, the parameter may be tumor growth.

According to the invention, combination treatment may be employed to increase the therapeutic effect of the anti-neoplastic agent, or LAG-3 protein, or derivative thereof, compared with the effect of the anti-neoplastic agent, or LAG-3 protein, or derivative thereof, as a monotherapy, or to decrease the doses of the individual components in the resulting combinations while preventing or further reducing the risk of unwanted or harmful side effects of the individual components.

In one embodiment, the LAG-3 protein, or derivative thereof, and the anti-neoplastic agent are each prescribed at a dose that is within a typically prescribed dose range for each compound as a monotherapy. The compounds may be prescribed as separate dosages or as a combination dosage. Such combinations provide increased efficacy compared with the effect of either compound as a monotherapy.

In another embodiment, the LAG-3 protein, or derivative thereof, and the anti-neoplastic agent are each prescribed at a dose that is below a typically prescribed dose for each component as a monotherapy, but at doses that have therapeutic efficacy in combination. The components may be prescribed as separate dosages or as a combination dosage. The dosages of the components in combination may be selected to provide a similar level of therapeutic efficacy as the LAG-3 protein, or derivative thereof, or the anti-neoplastic agent as a monotherapy, but with the advantage that the lower doses of the LAG-3 protein, or derivative thereof, and the anti-neoplastic agent reduce the risk of adverse side effects compared to the prescribed dosages of each compound as a monotherapy.

In another embodiment, the prescribed dosage of the anti-neoplastic agent is within a typically prescribed dose range for monotherapy, and the LAG-3 protein, or derivative thereof, is prescribed at a dosage that is below a typically prescribed dose for monotherapy.

In a further embodiment, the prescribed dosage of the anti-neoplastic agent is below a typically prescribed dose for monotherapy, and the LAG-3 protein, or derivative thereof, is prescribed at a dosage that is within a typically prescribed dose range for monotherapy.

Preferred dosages below the typically prescribed dose for monotherapy are doses that are up to 50%, or up to 25%, of the typically prescribed dose.

When administered in separate dosages, the LAG-3 protein, or derivative thereof, and the anti-neoplastic agent may be administered substantially simultaneously (for example, within about 60 minutes, about 50 minutes, about 40 minutes, about 30 minutes, about 20 minutes, about 10 minutes, about 5 minutes, or about 1 minute of each other) or separated in time by about 1 hour, about 2 hours, about 4 hours, about 6 hours, about 10 hours, about 12 hours, about 24 hours, about 36 hours, about 72 hours, or about 96 hours, or more.

The skilled person will be able to determine, and optimise, a suitable time course for sequential administration, depending on the particular combination of the LAG-3 protein, or derivative thereof, and the anti-neoplastic agent. The time course is preferably selected such that there is at least one beneficial effect, for example an enhancing of the effect of the LAG-3 protein, or derivative thereof, or the anti-neoplastic agent, or a mutual enhancing of the effect of the combination components, for example a more than additive effect, additional advantageous effects, fewer side effects, less toxicity, or a combined therapeutic effect compared with a non-effective dosage of one or both of the combination components, and very preferably a synergism of the combination components.

It will be appreciated that the optimum time course will depend on the factors such as the time taken for the peak plasma concentration of the compound to be reached after administration, and the elimination half-life of each compound. Preferably the time difference is less than the half-life of the first component to be administered.

The skilled person will also be able to determine appropriate timing for administration. In certain embodiments, the anti-neoplastic agent may be administered in the morning, and the LAG-3 protein, or derivative thereof, administered at least once later in the day. In other embodiments, the anti-neoplastic agent and LAG-3 protein, or derivative thereof, may be administered at substantially the same time.

In some embodiments, the anti-neoplastic agent may be administered to the subject, for example, by a medical practitioner, and the subject may be provided with a dose of the LAG-3 protein, or derivative thereof, for example in a pre-filled syringe, to administer later (for example later the same day, or the next day).

The subject may receive doses of the anti-neoplastic agent and LAG-3 protein, or derivative thereof, over a period of weeks, months, or years. For example, 1 week, 2 weeks, 3 weeks, 1 month, 2 months, 3 months, 4 months, 5 months, 6 months, 7 months, 8 months, 9 months, 10 months, 11 months, 1 year, 2 years, 3 years, 4 years, 5 years, or more.

Preferably the subject is a mammalian subject, more preferably a human subject.

Examples of cancers that may be treated according to the invention include breast, ovarian, lung, head, neck, endometrial, esophageal, bladder, cervical, osteogenic sarcoma, colon, colorectal cancer, lymphoma, and central nervous system or germ cell tumors.

In general, the components of a combination of the invention, or a composition of the invention, may be administered by known means, in any suitable formulation, by any suitable route. In some embodiments, the LAG-3 protein, or derivative thereof, is administered parenterally (including by subcutaneous, intravenous, or intramuscular injection). In some embodiments, the anti-neoplastic agent is administered intravenously. In particular embodiments, the LAG-3 protein, or derivative thereof, is administered subcutaneously, and the anti-neoplastic agent is administered intravenously.

Suitable pharmaceutical compositions and dosage forms may be prepared using conventional methods known to those in the field of pharmaceutical formulation and described in the relevant texts and literature, for example, in Remington: The Science and Practice of Pharmacy (Easton, Pa.: Mack Publishing Co., 1995).

It is especially advantageous to formulate combinations or compositions of the invention in unit dosage form for ease of administration and uniformity of dosage. The term "unit dosage forms" as used herein refers to physically discrete units suited as unitary dosages for the individuals to be treated. That is, the compositions are formulated into discrete dosage units each containing a predetermined, "unit dosage" quantity of an active agent calculated to produce the desired therapeutic effect in association with the required pharmaceutical carrier. The specifications of unit dosage forms of the invention are dependent on the unique characteristics of the active agent to be delivered. Dosages can further be determined by reference to the usual dose and manner of administration of the ingredients. It should be noted that, in some cases, two or more individual dosage units in combination provide a therapeutically effective amount of the active agent, for example, two tablets or capsules taken together may provide a therapeutically effective dosage, such that the unit dosage in each tablet or capsule is approximately 50% of the therapeutically effective amount.

Preparations according to the invention for parenteral administration include sterile aqueous and non-aqueous solutions, suspensions, and emulsions. Injectable aqueous solutions contain the active agent in water-soluble form. Examples of non-aqueous solvents or vehicles include fatty oils, such as olive oil and corn oil, synthetic fatty acid esters, such as ethyl oleate or triglycerides, low molecular weight alcohols such as propylene glycol, synthetic hydrophilic polymers such as polyethylene glycol, liposomes, and the like. Parenteral formulations may also contain adjuvants such as solubilizers, preservatives, wetting agents, emulsifiers, dispersants, and stabilizers, and aqueous suspensions may contain substances that increase the viscosity of the suspension, such as sodium carboxymethyl cellulose, sorbitol, and dextran. Injectable formulations may be rendered sterile by incorporation of a sterilizing agent, filtration through a bacteria-retaining filter, irradiation, or heat. They can also be manufactured using a sterile injectable medium. The active agent may also be in dried, e.g., lyophilized, form that may be rehydrated with a suitable vehicle immediately prior to administration via injection.

In addition to the formulations described previously, the active agent may be formulated as a depot preparation for controlled release of the active agent, preferably sustained release over an extended time period. These sustained release dosage forms are generally administered by implantation (for example, subcutaneously or intramuscularly or by intramuscular injection).

Combined preparations of the invention may be packaged with instructions for administration of the components on the combination. The instructions may be recorded on a suitable recording medium or substrate. For example, the instructions may be printed on a substrate, such as paper or plastic. The instructions may be present as a package insert, in the labeling of the container or components thereof (i.e., associated with the packaging or sub-packaging). In other embodiments, the instructions are present as an electronic storage data file present on a suitable computer readable storage medium, for example, CD-ROM, diskette. Some or all components of the combined preparation may be packaged in suitable packaging to maintain sterility.

Embodiments of the invention are described in the examples below, with reference to the accompanying drawings in which.

FIG. 13 shows amino acid sequence of mature human LAG-3 protein. The four extracellular Ig superfamily domains are at amino acid residues: 1-149 (D1); 150-239 (D2); 240-330 (3); and 331-412 (04). The amino acid sequence of the extra-loop structure of the D1 domain of human LAG-3 protein is shown underlined in bold.

EXAMPLE 1

Effect of Administration of a LAG-3 Derivative and a Topoisomerase I Inhibitor in the Treatment of Cancer A murine syngeneic skin tumour model was established using the colorectal adenocarcinoma cell line CT26.

One quarter of the minimum tumorigenic dose (MTD) of tumour cells ($0.5 \times 10^5$ cells) was implanted by subcutaneous (s.c.) injection in the right flank of four groups of BALB/c mice (5 weeks old) at Day 0. The mice were injected with phosphate buffered saline (PBS) (Group 1 mice), the LAG-3 derivative IMP321 (Group 2 mice), IMP321 and Topotecan (Group 3 mice), or Topotecan alone (Group 4 mice) according to the following schedule:

Group 1 (8 mice): negative control: PBS s.c. injection at D11, D14, D18, D21, D25 and D28;

Group 2 (7 mice): IMP321 s.c. injection (50 μg, 1.9 mg/ml) at D11, D14, D18, D21, D25 and D28;

Group 3 (8 mice): IMP321 s.c. injection (50 μg, 1.9 mg/ml) at D11, D14, D18, D21, D25 and D28, plus Topotecan i.p. injection (45 μg, 2.5 mg/kg) at D10, D13 and D17;

Group 4 (8 mice): Topotecan i.p. injection (45 μg, 2.5 mg/kg) at D10, D13 and D17.

Figure 1:
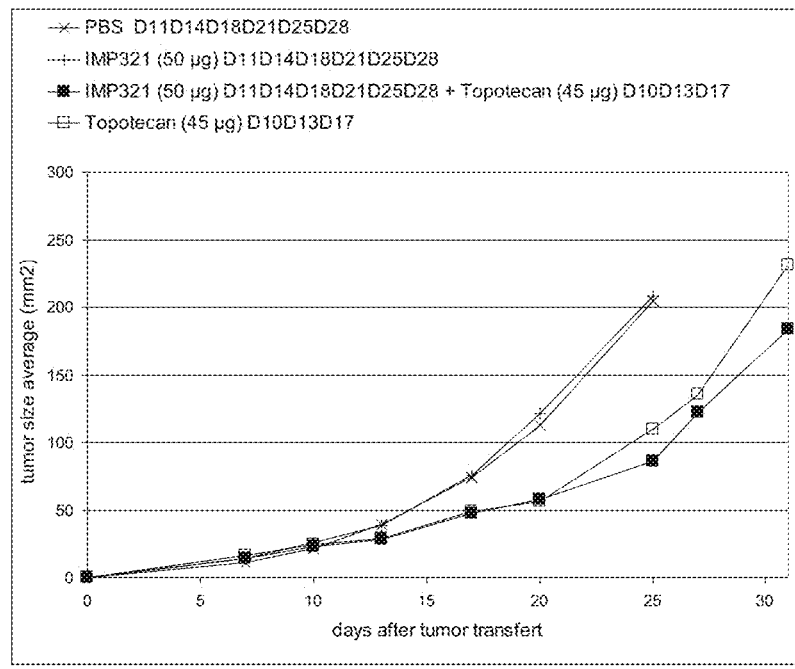
FIG. 1 shows the effect of administration of a LAG-3 derivative and Topotecan in the treatment of cancer.

Tumour growth was monitored twice a week by measuring two perpendicular tumour diameters using calipers. The results are shown in FIG. 1. Tumour size means the cross-sectional area in $mm^2$.

The results show that IMP321 alone had no effect on tumour growth, topotecan had some effect on reducing tumor growth, but combined treatment with IMP321 and topotecan has a greater (i.e. a synergistic) effect.

EXAMPLE 2

Effect of Administration of a LAG-3 Derivative and a Platinum-Based Anti-Neoplastic Agent in the Treatment of Cancer A murine syngeneic skin tumour model was established using the lymphoma cell line EL4.

The minimum tumorigenic dose (MTD) of tumour cells ($5 \times 10^5$ cells) was implanted by s.c. injection in the right flank of C57Bl/6 mice (5 weeks old) at Day 0. The mice were injected with phosphate buffered saline (PBS) (Group 1 mice), IMP321 (Group 2 mice), IMP321 and Carboplatin (Group 3 mice), or Carboplatin alone (Group 4 mice) according to the following schedule:
  Group 1 (8 mice): negative control: PBS s.c. injection at D7, D11, D14, D19, D21 and D24;
  Group 2 (8 mice): IMP321 s.c. injection (50 µg, 3.96 mg/ml) at D7, D11, D14, D19, D21 and D24;
  Group 3 (8 mice): IMP321 s.c. injection (50 µg, 3.96 mg/m) at D7, D11, D14, D19, D21 and D24, plus Carboplatin i.p. injection (288 µg, 16 mg/kg) at D6, D10, D13 and D17;
  Group 4 (8 mice): Carboplatin i.p. injection (288 µg, 16 mg/kg) at D6, D10, D13 and D17.

Figure 2:
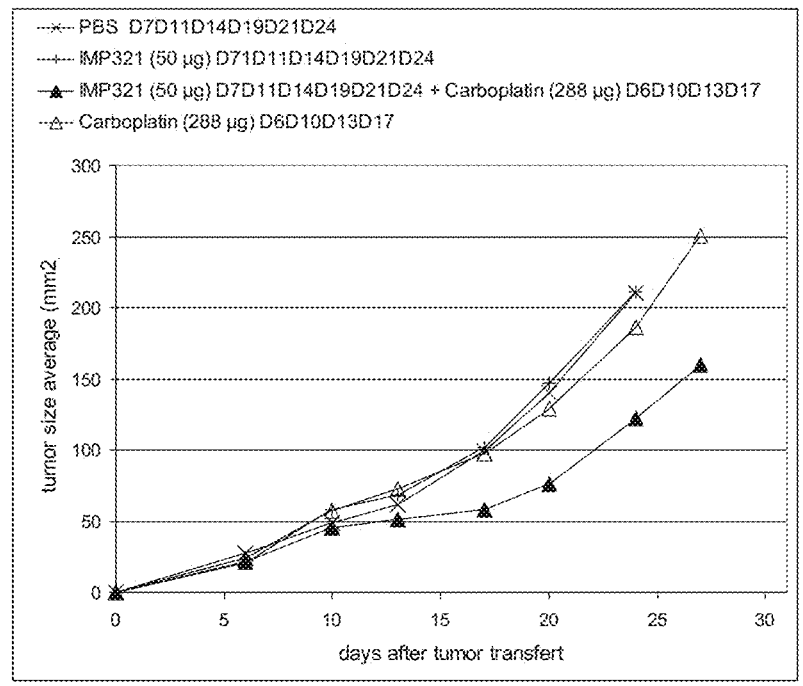
FIG. 2 shows the effect of administration of a LAG-3 derivative and Carboplatin in the treatment of cancer.

Tumour growth was monitored twice a week by measuring two perpendicular tumour diameters using calipers. The results are shown in FIG. 2. Tumour size means the cross-sectional area in $mm^2$.

The results show that IMP321 alone had no effect on tumour growth, carboplatin alone had very little effect, if any, but combined treatment with IMP321 and carboplatin reduced tumour growth, thereby demonstrating a synergistic effect of the combined administration.

EXAMPLE 3

Effect of Administration of a LAG-3 Derivative and Different Platinum-Based Anti-Neoplastic Agents in the Treatment of Cancer A murine syngeneic skin tumour model was established using the lymphoma cell line EL4.

The minimum tumorigenic dose (MTD) of tumour cells ($5 \times 10^5$ cells) was implanted by s.c. injection in the right flank of C57Bl/6 mice (5 weeks old) at Day 0. The mice were injected with phosphate buffered saline (PBS) (Group 1 mice), IMP321 (Group 2 mice), IMP321 and Carboplatin (Group 3 mice), Carboplatin alone (Group 4 mice), IMP321 and Oxaliplatin (Group 5 mice), or Oxaliplatin alone (Group 6 mice) according to the following schedule:
  Group 1 (10 mice): negative control: PBS s.c. injection at D7, D11, D14, D18, D21 and D25;
  Group 2 (10 mice): IMP321 s.c. injection (50 µg, 1.9 mg/m) at D7, D11, D14, D18, D21 and D25;
  Group 3 (9 mice): IMP321 s.c. injection (50 µg, 1.9 mg/ml) at D7, D11, D14, D18, D21 and D25, plus Carboplatin i.p. injection (288 µg, 16 mg/kg) at D6, D10, D13 and D17;
  Group 4 (10 mice): Carboplatin i.p. injection (288 µg, 16 mg/kg) at D6, D10, D13 and D17;
  Group 5 (10 mice): IMP321 s.c. injection (50 µg, 1.9 mg/m) at D7, D11, D14, D18, D21 and D25, plus Oxaliplatin i.p. injection (54 µg, 3 mg/kg) at D6 and D10;
  Group 6 (10 mice): Oxaliplatin i.p. injection (54 µg, 3 mg/kg) at D6 and D10.

Figure 3A:
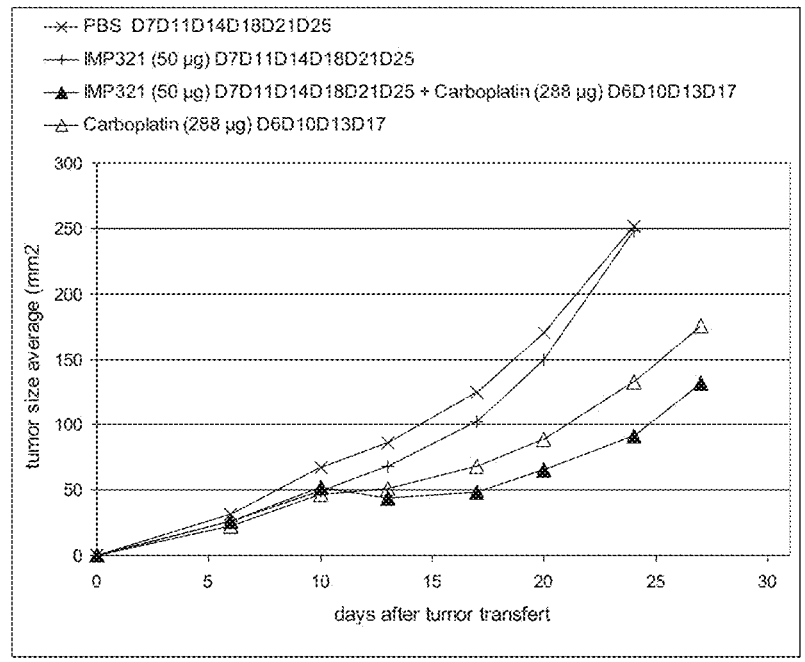
FIGS. 3A-3B shows the effect of administration of (A) a LAG-3 derivative and Carboplatin, or (B) a LAG-3 derivative and Oxaliplatin in the treatment of cancer.
Figure 3B:
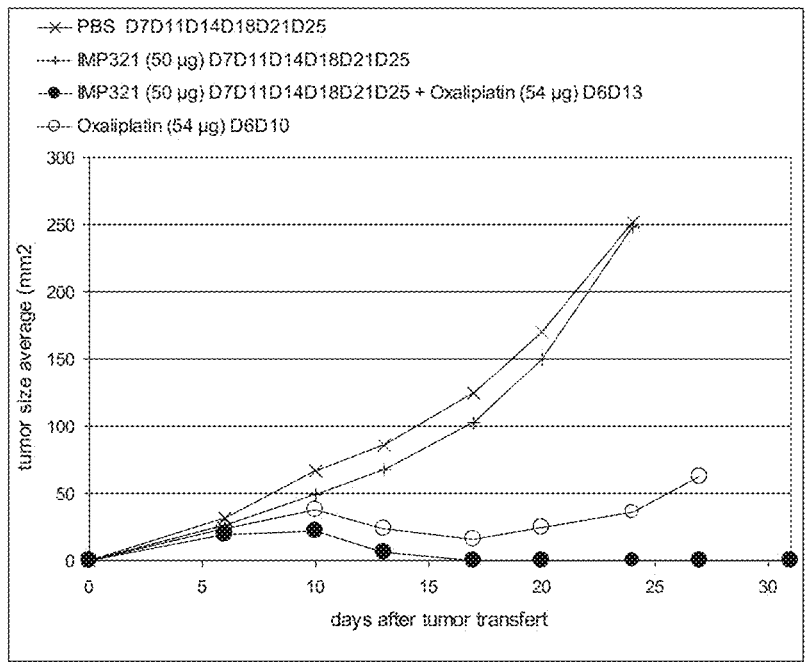

Tumour growth was monitored twice a week by measuring two perpendicular tumor diameters using calipers. The results are shown in FIG. 3A (for Carboplatin) and FIG. 3B (for Oxaliplatin). Tumour size means the cross-sectional area in $mm^2$.

The results show that IMP321 alone had little, if any effect, carboplatin alone had some effect, and combined treatment with IMP321 and carboplatin had a greater (i.e. a synergistic) effect. Oxaliplatin alone had an effect, but combined treatment with IMP321 and oxaliplatin had an even greater (i.e. a synergistic) effect, with tumour growth completely inhibited by Day 17.

EXAMPLE 4

Effect of Administration of a LAG-3 Derivative and a Platinum-Based Anti-Neoplastic Agent in the Treatment of Cancer The effect of combined treatment with the LAG-3 derivative IMP321 (also referred to as hLAG-3Ig) and oxaliplatin in the C38 colon adenocarcinoma tumor model was evaluated. In this model, tumor fragments are surgically implanted subcutaneously. When treatment is begun (at day 12, when the mean tumor volume is 200 mm), the tumor is relatively mature and so provides a good model for real-life tumors.

Mouse colon 38 (C38) tumor fragments were obtained frozen from the Division of Cancer Treatment, Tumor Repository, NCI (Frederick, MD, USA). The C38 fragments were stored frozen in DMSO/SVF/RPMI 1640 medium (10/10/80) in liquid nitrogen until use. The fragments were thawed at 37° C. for 5 min, rinsed twice in RPMI 1640 medium before subcutaneous (SC) implantation in mice. The C38 tumors were serially transplanted in C57Bl/6 mice.

Small C38 tumor fragments (20-30 mg) were subcutaneously implanted in the right flank of 12 C57BL/6 mice. When tumor sizes reached 500-1000 $mm^3$, tumors were surgically excised and small C38 tumor fragments (20-30 mg) were subcutaneously implanted in the right flank of recipient C57BL/6 mice.

Treatment started when the tumors reached a mean volume of 200-300 $mm^3$. The treatment schedule was as follows:
  Group 1 (10 mice): one weekly SC injection of PBS for 4 consecutive weeks;
  Group 2 (10 mice): one weekly IV injection of oxaliplatin at 5 mg/kg/inj for 4 consecutive weeks;
  Group 3 (10 mice): one weekly SC injection of 20 µg IMP321 for 4 consecutive weeks:
  Group 4 (10 mice): one weekly IV injection of oxaliplatin at 5 mg/kg/inj in combination with one weekly SC injection of 20 µg IMP321 for 4 consecutive weeks.

Treatment started at day 12 (D12) when the different groups had a mean tumor volume of 200 $mm^3$. PBS or Oxaliplatin was injected at D12, D19, D26 and D33. IMP321 was injected the day after Oxaliplatin, that is at D13, D20, 27 and D34. Animals were terminated when the subcutaneous tumor reached a maximum volume of 2,000 $mm^3$:

| Group | Treatment | Dose | Administration route | Treatment schedule |
|-------|-----------|------|----------------------|--------------------|
| 1 | PBS | — | SC | Q7Dx4 |
| 2 | Oxaliplatin | 5 mg/kg/inj | IV | Q7Dx4 |
| 3 | IMP321 | 20 µg/mouse/inj | SC | Q7Dx4* |
| 4 | Oxaliplatin | 5 mg/kg/inj | IV | Q7Dx4 |
|   | IMP321 | 20 µg/mouse/inj | SC | Q7Dx4* |

*performed the day after the treatment with oxaliplatin

Figure 4A:
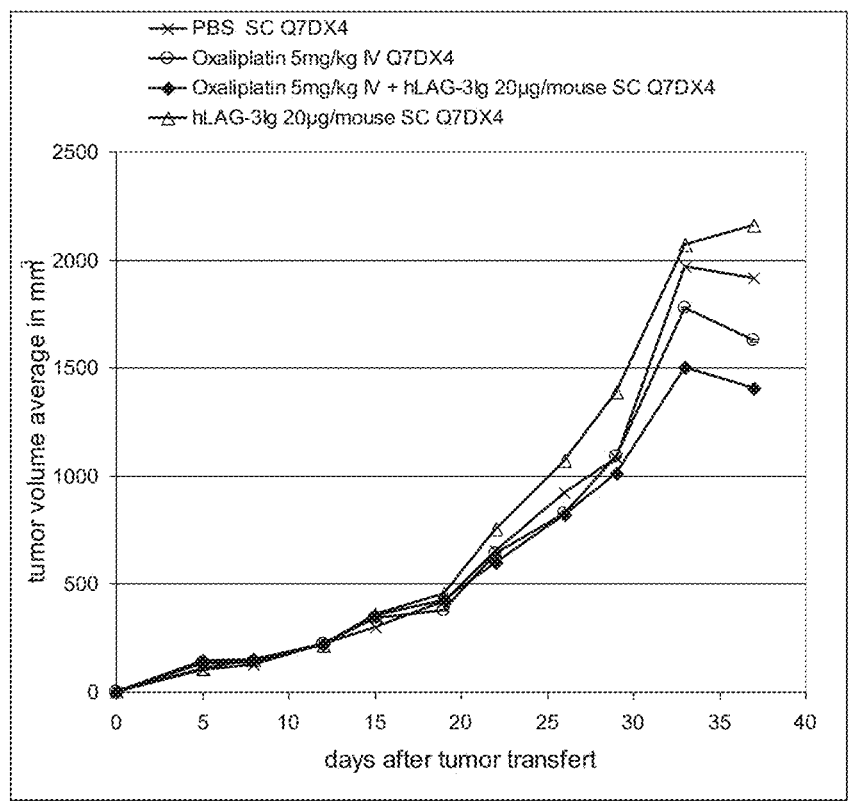
FIGS. 4A-4B shows the effect of administration of a LAG-3 derivative and Oxaliplatin in the treatment of cancer: (A) shows the effect on tumor size, and (B) shows the effect on survival.
Figure 4B:
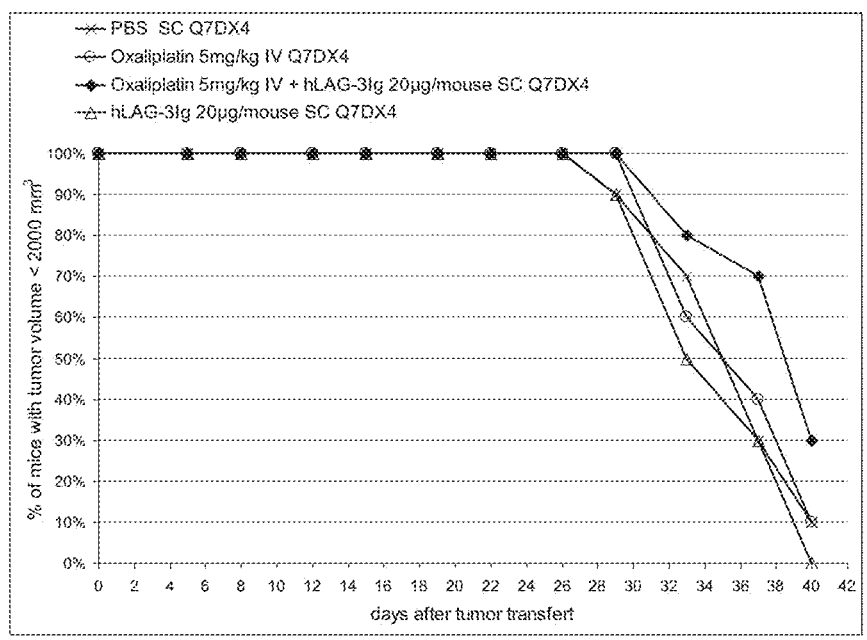

The results are shown in FIG. 4A. The results show that IMP321 alone had no effect on delaying tumor growth. Oxaliplatin had a slight effect. The combination of Oxaliplatin and IMP321 had a greater effect. The same synergistic effect is seen in the survival curves, shown in FIG. 4B.

EXAMPLE 5

Binding of LAG-3 Derivatives to MHC Class II-Positive Cells

Several derivatives of LAG-3 were tested for their ability to bind to MHC class II-positive cells:
i) domains D1-D4 of LAG-3 linked to immunoglobulin Fc (Ig Fc) sequence by a first linker (LAG-3 D1D4-linker1-Ig, sLAG-3 D1D4-Ig, or IMP321);
ii) domains D1-D4 of LAG-3, linked to Ig Fc sequence by a second linker (LAG-3 D1D4-linker2-Ig, or sLAG-3 D1D4-llinkerB-Ig);
iii) domains D1 and D2 of LAG-3, linked to Ig Fc sequence by the second linker (LAG-3 D1D2-linker2-Ig, or sLAG-3 D1D2-linkerB-Ig); and
iv) domains D1-D4 of LAG-3 linked to Ig Fc sequence by the first linker, but with a mutation in the MHC class II binding site of the D1 domain of LAG-3, at position R75 (R75A), which enhances binding to MHC class II molecules by three-fold or more (Huard et al., Proc. Natl. Acad. Sci. USA, 1997, 94:5744) (IMP321 R75A).

Figure 5:
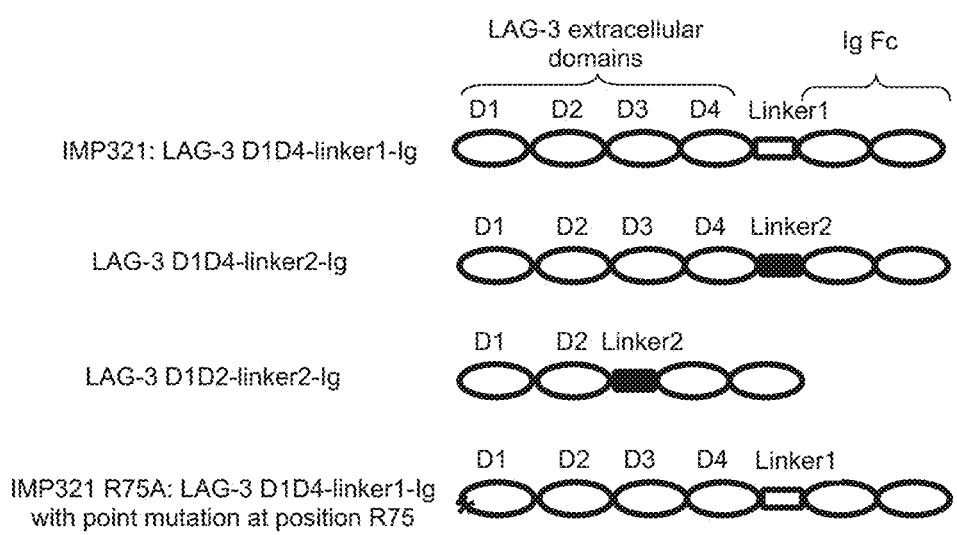
FIG. 5 shows an illustration of derivatives of LAG-3 protein fused to Immunoglobulin Fc (IgFc) sequence.

The derivatives are illustrated in FIG. 5.

Figure 6:
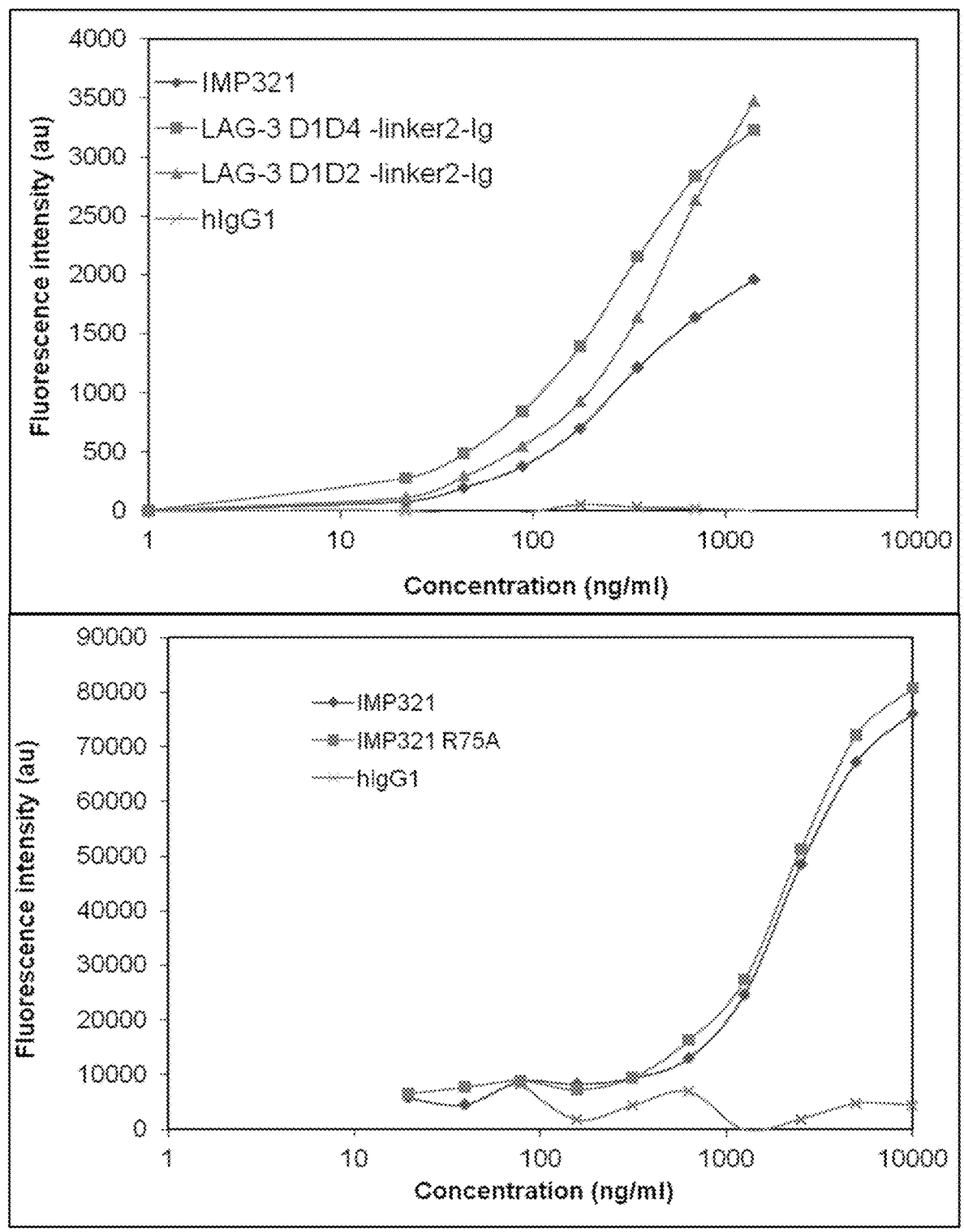
FIG. 6 shows binding of LAG-3 derivatives to MHC class II-positive cells.

MHC class II+ Raji cells were incubated for 45 minutes at 4° C. with various concentrations of the LAG-3 derivatives, or with a human IgG1 antibody (hIgG1) as a negative control. The LAG-3 molecules bound to the cell surface were revealed with a FITC-conjugated goat anti-mouse Ig (Coulter). The cells were analyzed by flow cytometry. The results, expressed as fluorescence intensity units, are shown in FIG. 6. The results show that all of the LAG-3 derivatives bound to MHC class II-positive cells.

EXAMPLE 6

Figure 7:
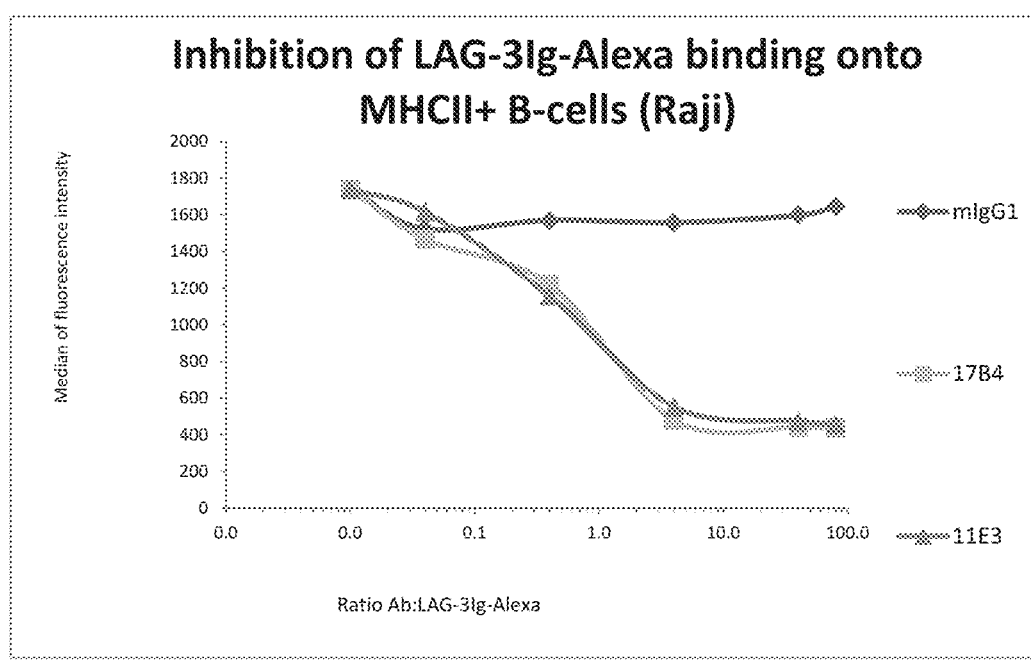
FIG. 7 shows inhibition of binding of a LAG-3 derivative to MHC class II-positive cells by antibodies that block binding of LAG-3 to MHC class II molecules.

Inhibition of Binding of the LAG-3 Derivative IMP321 to MHC Class II-Positive Cells by Antibodies that Block Binding of LAG-3 to MHC Class II Molecules 17B4 and 11E3 are anti-LAG-3 monoclonal antibodies that are known to block binding of LAG-3 to MHC class II molecules. Binding of an IMP321-label conjugate (LAG-3Ig-Alexa 488) to MHC class II-positive B cells (Raji cells) was determined following pre-incubation of the conjugate (4 µg/ml at 4° C.) with 17B4 or 11E3 blocking antibody, or with an isotype-matched negative control monoclonal antibody (mIgG1). Analysis of cell-bound fluorescence was carried out using fluorescence-activated cell sorting (FACS). The results are shown in FIG. 7.

The results show that binding of IMP321 to Raji cells was inhibited by LAG-3-specific monoclonal antibody that blocks binding of LAG-3 to MHC class II molecules.

EXAMPLE 7

Activation of Monocytes by LAG-3 Derivatives

Figure 8:
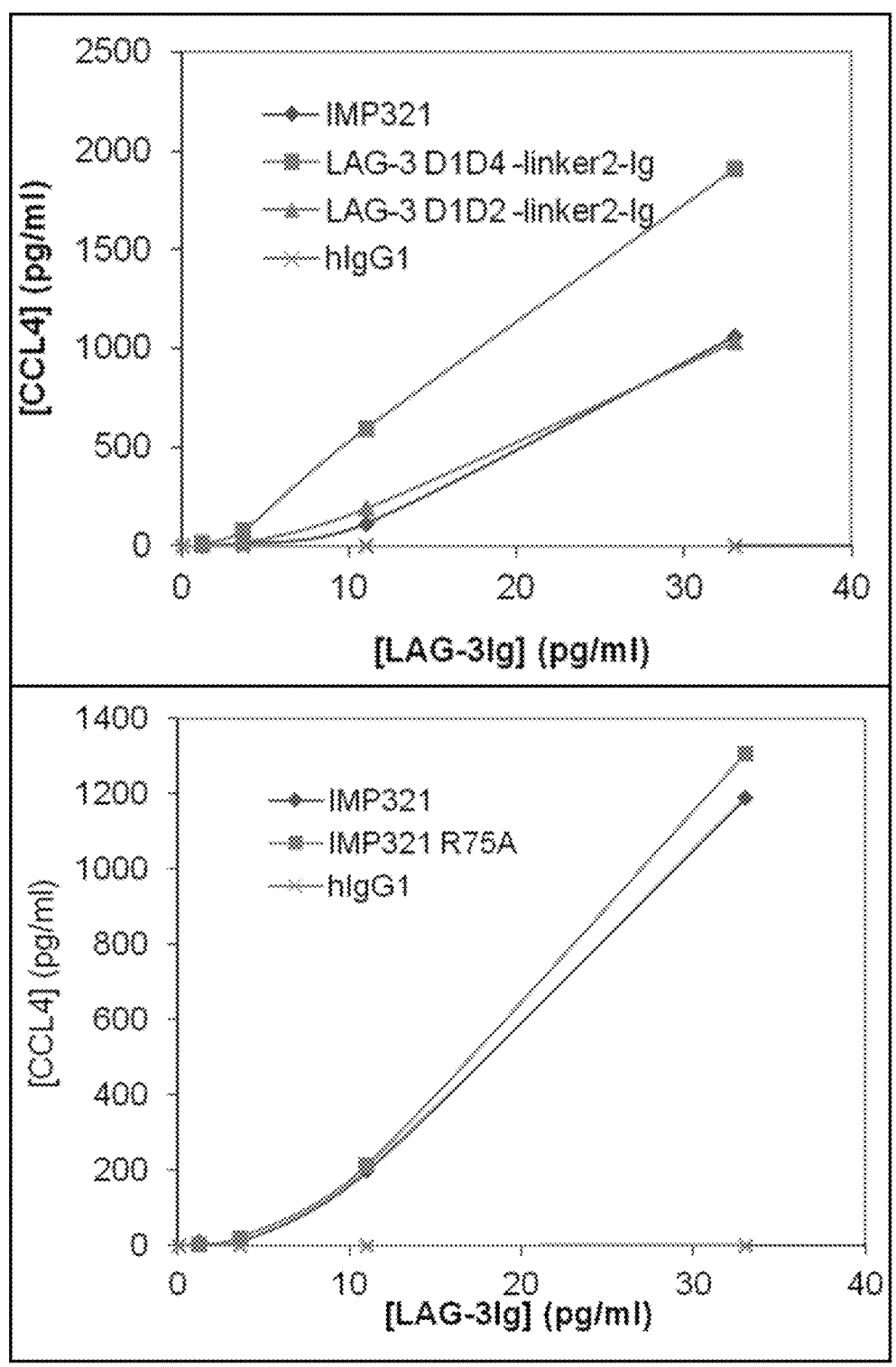
FIG. 8 shows activation of THP-1 cells by LAG-3 derivatives, as determined by CCL4 secretion.
Figure 9:
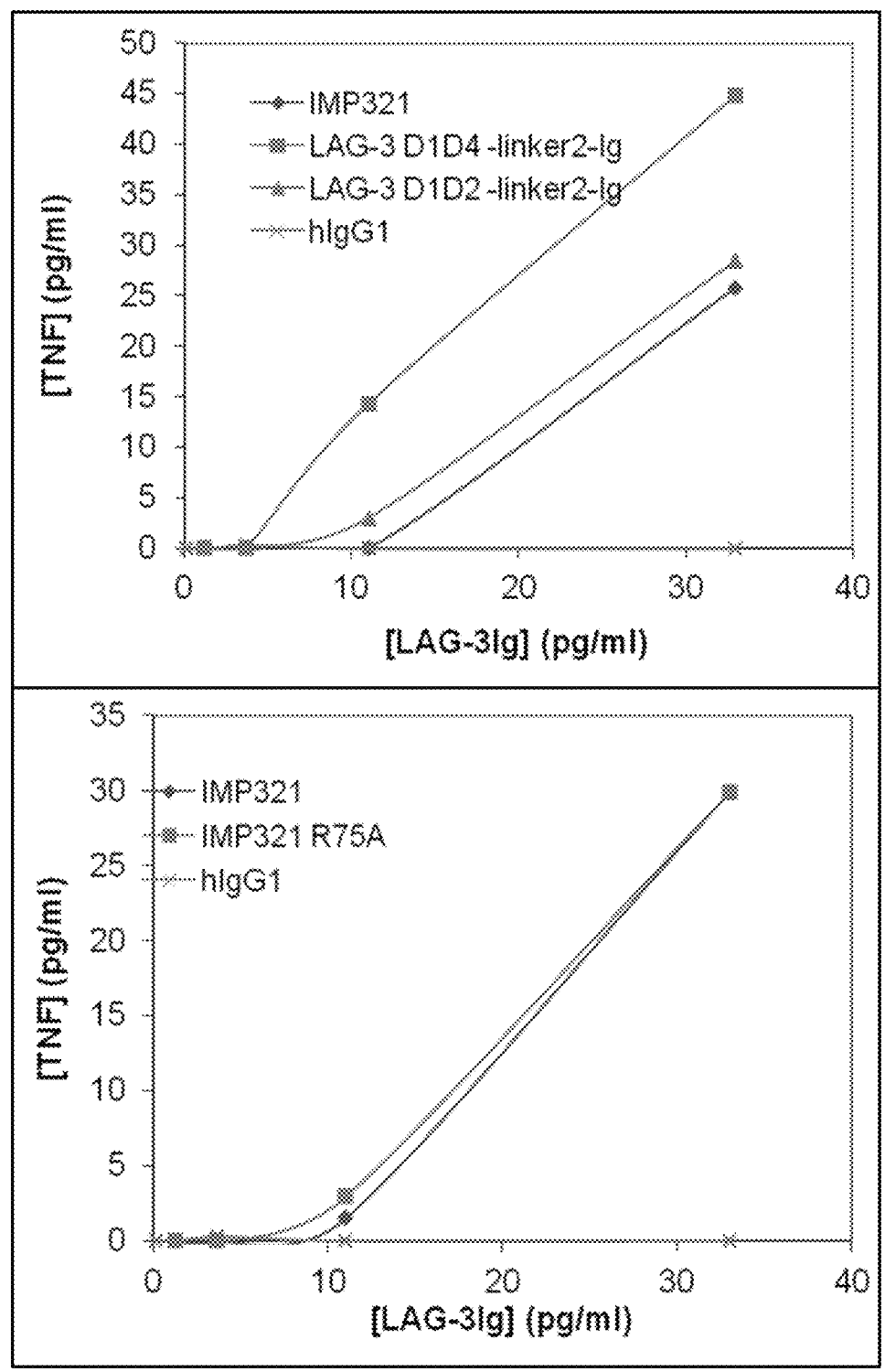
FIG. 9 shows activation of THP-1 cells by LAG-3 derivatives, as determined by TNF-α secretion.

THP-1 cells were incubated for 4 hours at 4° C. with the LAG-3 derivatives illustrated in FIG. 5, or with human IgG1 as a negative control. The amount of secretion by the THP-1 cells of the chemokine CCL4, and the cytokine Tumor Necrosis Factor-α, TNF-α, was determined, and was used as a measure of monocyte activation. CCL4 and TNF-α secretion was quantified in the cell supernatants using a Cytometric Beads Array. The results of the CCL4 determinations are shown in FIG. 8, and the results of the TNF-α determinations are shown in FIG. 9.

The results show that the LAG-3 derivates were all able to activate THP-1 monocytic cells.

EXAMPLE 8

Figure 10:
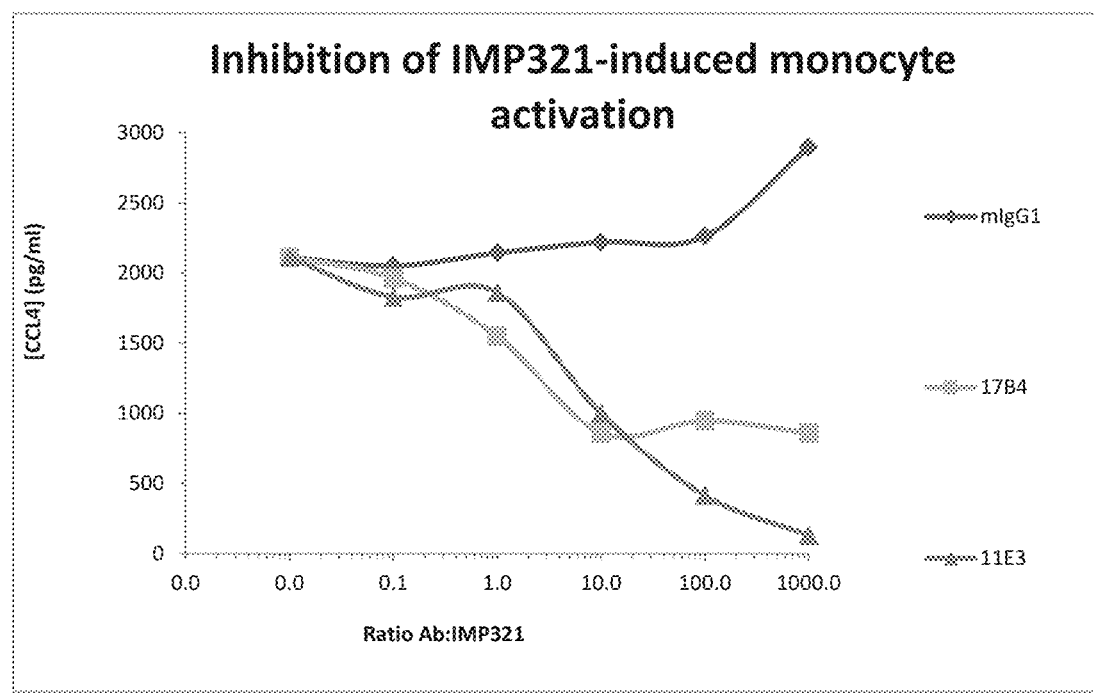
FIG. 10 shows inhibition of LAG derivative-induced monocyte activation by antibodies that block binding of LAG-3 to MHC class II molecules.
Figure 10:
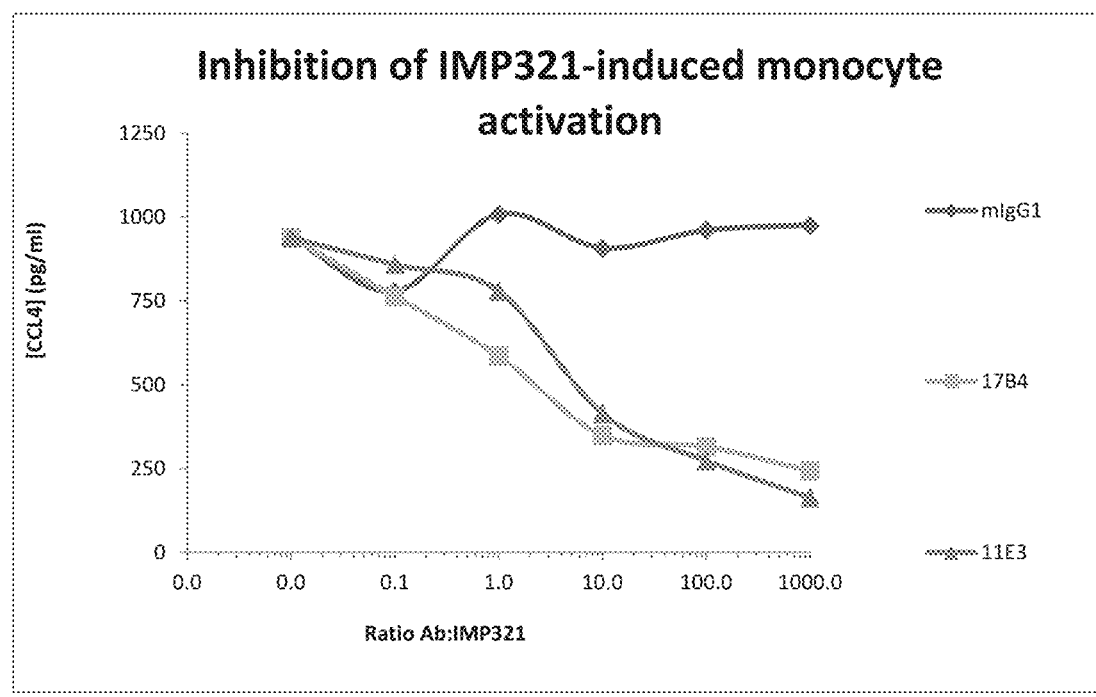

Inhibition of IMP321-Induced Monocyte Activation by Antibodies that Block Binding of LAG-3 to MHC Class II Molecules IMP321 (20 ng/ml) was preincubated with 17B4 or 11E3 antibody (at +37° C.), before incubation of the mixture with THP-1 cells for 4 hours. The amount of CCL4 secretion by the THP-1 cells was used to determine the level of monocyte activation. The results of two experiments are shown in FIG. 10.

The results demonstrate that IMP321-induced monocyte activation is inhibited by the blocking anti-LAG-3 mAbs 17B4 and 11E3. This indicates that the ability of IMP321 to activate monocytes is dependent on binding of IMP321 to MHC class II molecules.

EXAMPLE 9

Activation of Primary Antigen-Presenting Cells (APCs) by LAG-3 Derivatives

Figure 11:
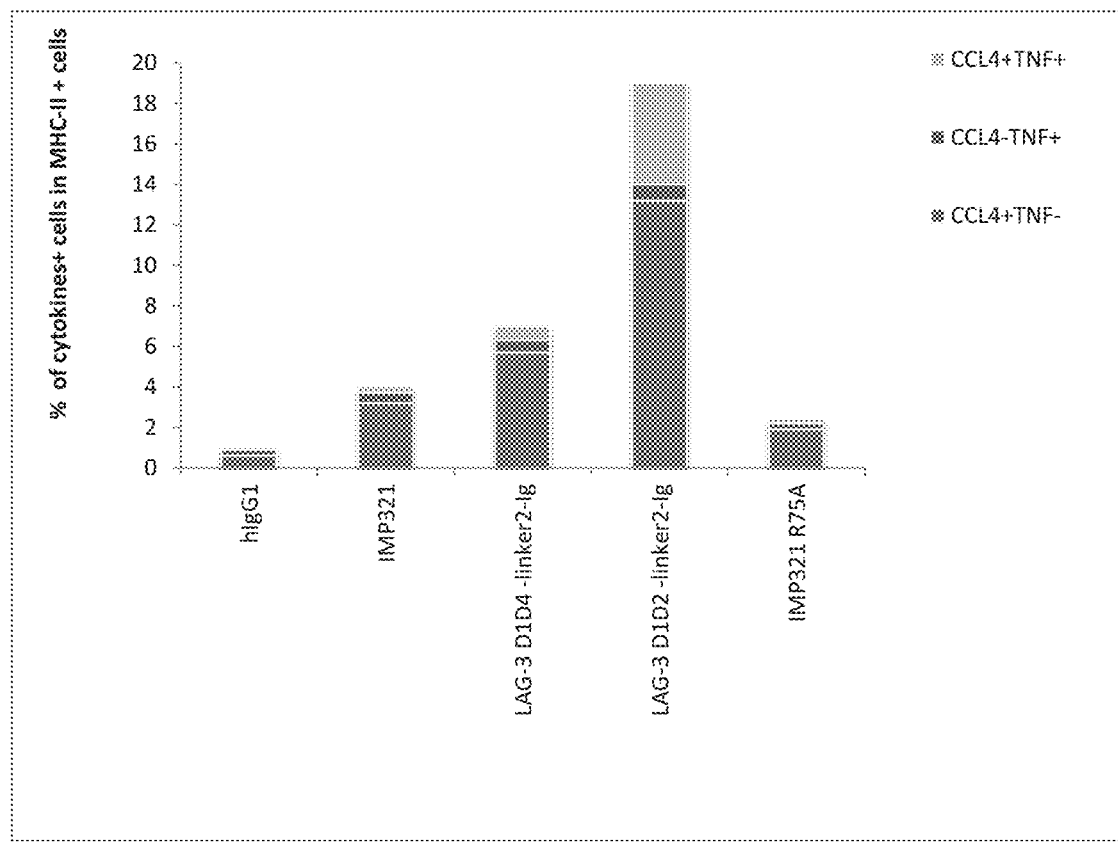
FIG. 11 shows activation of antigen-presenting cells (APCs) by LAG-3 derivatives.

Human peripheral blood mononuclear cells (PBMCs) were incubated for 4 hours with the LAG-3 derivatives illustrated in FIG. 5, or with human IgG1 as a negative control, in the presence of brefeldin, a secretion inhibitor. The cytokine response of the APCs present in the PBMCs was determined by intracellular staining of CCL4, a chemokine known to favour the Th1 and CD8-positive response, and TNF-α, a multifunctional cytokine which directly inhibits tumorigenesis. The results were analyzed by cytometry. The results, represented by the percentage of cells expressing CCL4 and/or TNF-α in MHC class II-positive cells, are shown in FIG. 11.

The results show that all the LAG-3 derivatives tested induced the production of CCL4, and TNF-α.

EXAMPLE 10

Activation of T Cells by LAG-3 Derivatives

Figure 12:
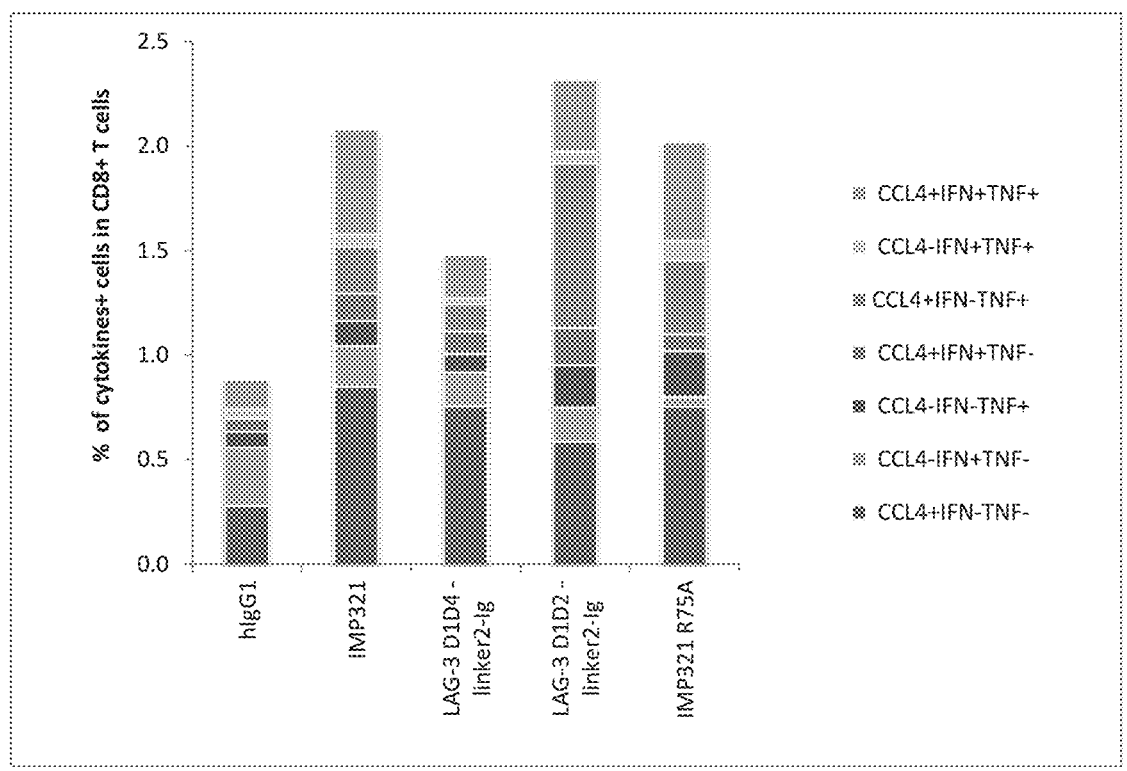
FIG. 12 shows activation of CD8-positive T cells by LAG-3 derivatives.

Human PBMCs were incubated for 18 hours with the LAG-3 derivatives illustrated in FIG. 5, or with human IgG1 as a negative control. Brefeldin was present for the last 16 hours of the incubation. The cytokine response of CD8-positive T cells after 18 hour exposure to LAG-3 derivatives was followed by intracellular staining of CCL4, IFN-γ and TNF-α and analyzed by cytometry. The results, represented as the percentage of cells expressing CCL4, IFN-γ and/or TNF-α in CD3-positive/CD8-positive T cells, are shown in FIG. 12.

The results show that all of the LAG-3 derivatives tested induced activation of Type 1 cytotoxic CD8-positive T cells (Tc1 cells). It is concluded that, through binding to MHC class II molecules expressed by APCs, the LAG-3 derivatives induced activation of Tc1 cells. Activation of Tc1 cells forms the main anti-tumor immune response.

The invention claimed is:

1. A method of treating or ameliorating a cancer, which comprises:
   administering to a subject in need of such treatment or amelioration an effective amount of:
   a derivative of LAG-3 protein that is able to bind to MHC class II molecules, wherein the derivative comprises domains D1 and D2 of human LAG-3 protein, and wherein the derivative is fused to an Immunoglobulin Fc sequence; and
   an anti-neoplastic agent, wherein the anti-neoplastic agent is a platinum-based anti-neoplastic agent or a topoisomerase I inhibitor; and
   synergistically reducing tumor growth in the subject, the synergistic reduction of tumor growth being more than a sum of a reduction of tumor growth caused by administration to the subject of the derivative alone and the anti-neoplastic agent alone.

2. A method according to claim 1, wherein the derivative and the anti-neoplastic agent are administered sequentially to the subject.

3. A method according to claim 1, wherein the derivative is administered after the anti-neoplastic agent.

4. A method according to claim 2, wherein the derivative and the anti-neoplastic agent are administered to the subject within 96 hours of each other.

5. A method according to claim 1, wherein the derivative and the anti-neoplastic agent are co-administered to the subject.

6. A method according to claim 1, wherein the derivative is administered to the subject at a dose which is a molar equivalent of 0.25-30 mg of LAG-3Ig fusion protein IMP321 per individual.

7. A method according to claim 1, wherein a plurality of doses of the derivative is administered to the subject.

8. A method according to claim 1, wherein a plurality of doses of the anti-neoplastic agent is administered to the subject.

9. A method according to claim 1, wherein a dose of the derivative is administered before, with, or after each administration of two or more doses of the anti-neoplastic agent.

10. A method according to claim 1, wherein the derivative comprises domains D1, D2, D3, and optionally D4 of human LAG-3 protein.

11. A method according to claim 1, wherein the derivative of LAG-3 protein is IMP321.

12. A method according to claim 1, wherein the anti-neoplastic agent is selected from the group consisting of oxaliplatin, carboplatin, and topotecan.

* * * * *

SEQUENCE LISTING

<160> NUMBER OF SEQ ID NOS: 2

<210> SEQ ID NO 1
<211> LENGTH: 502
<212> TYPE: PRT
<213> ORGANISM: Homo sapiens

<400> SEQUENCE: 1

```
Leu Gln Pro Gly Ala Glu Val Pro Val Val Trp Ala Gln Glu Gly Ala
1               5                   10                  15

Pro Ala Gln Leu Pro Cys Ser Pro Thr Ile Pro Leu Gln Asp Leu Ser
            20                  25                  30

Leu Leu Arg Arg Ala Gly Val Thr Trp Gln His Gln Pro Asp Ser Gly
        35                  40                  45

Pro Pro Ala Ala Ala Pro Gly His Pro Leu Ala Pro Gly Pro His Pro
    50                  55                  60

Ala Ala Pro Ser Ser Trp Gly Pro Arg Pro Arg Arg Tyr Thr Val Leu
65                  70                  75                  80

Ser Val Gly Pro Gly Gly Leu Arg Ser Gly Arg Leu Pro Leu Gln Pro
                85                  90                  95

Arg Val Gln Leu Asp Glu Arg Gly Arg Gln Arg Gly Asp Phe Ser Leu
            100                 105                 110

Trp Leu Arg Pro Ala Arg Arg Ala Asp Ala Gly Glu Tyr Arg Ala Ala
        115                 120                 125

Val His Leu Arg Asp Arg Ala Leu Ser Cys Arg Leu Arg Leu Arg Leu
    130                 135                 140

Gly Gln Ala Ser Met Thr Ala Ser Pro Pro Gly Ser Leu Arg Ala Ser
145                 150                 155                 160

Asp Trp Val Ile Leu Asn Cys Ser Phe Ser Arg Pro Asp Arg Pro Ala
                165                 170                 175

Ser Val His Trp Phe Arg Asn Arg Gly Gln Gly Arg Val Pro Val Arg
            180                 185                 190

Glu Ser Pro His His Leu Ala Glu Ser Phe Leu Phe Leu Pro Gln
            195                 200                 205

Val Ser Pro Met Asp Ser Gly Pro Trp Gly Cys Ile Leu Thr Tyr Arg
    210                 215                 220

Asp Gly Phe Asn Val Ser Ile Met Tyr Asn Leu Thr Val Leu Gly Leu
225                 230                 235                 240

Glu Pro Pro Thr Pro Leu Thr Val Tyr Ala Gly Ala Gly Ser Arg Val
                245                 250                 255

Gly Leu Pro Cys Arg Leu Pro Ala Gly Val Gly Thr Arg Ser Phe Leu
            260                 265                 270

Thr Ala Lys Trp Thr Pro Pro Gly Gly Gly Pro Asp Leu Leu Val Thr
        275                 280                 285

Gly Asp Asn Gly Asp Phe Thr Leu Arg Leu Glu Asp Val Ser Gln Ala
    290                 295                 300

Gln Ala Gly Thr Tyr Thr Cys His Ile His Leu Gln Glu Gln Gln Leu
305                 310                 315                 320

Asn Ala Thr Val Thr Leu Ala Ile Ile Thr Val Thr Pro Lys Ser Phe
                325                 330                 335

Gly Ser Pro Gly Ser Leu Gly Lys Leu Leu Cys Glu Val Thr Pro Val
            340                 345                 350

Ser Gly Gln Glu Arg Phe Val Trp Ser Ser Leu Asp Thr Pro Ser Gln
        355                 360                 365
```

-continued

```
Arg Ser Phe Ser Gly Pro Trp Leu Glu Ala Gln Glu Ala Gln Leu Leu
    370                 375                 380

Ser Gln Pro Trp Gln Cys Gln Leu Tyr Gln Gly Glu Arg Leu Leu Gly
385                 390                 395                 400

Ala Ala Val Tyr Phe Thr Glu Leu Ser Ser Pro Gly Ala Gln Arg Ser
                405                 410                 415

Gly Arg Ala Pro Gly Ala Leu Pro Ala Gly His Leu Leu Leu Phe Leu
            420                 425                 430

Thr Leu Gly Val Leu Ser Leu Leu Leu Val Thr Gly Ala Phe Gly
        435                 440                 445

Phe His Leu Trp Arg Arg Gln Trp Arg Pro Arg Arg Phe Ser Ala Leu
    450                 455                 460

Glu Gln Gly Ile His Pro Gln Ala Gln Ser Lys Ile Glu Glu Leu Glu
465                 470                 475                 480

Gln Glu Pro Glu Pro Glu Pro Glu Pro Glu Pro Glu Pro Glu Pro Glu
                485                 490                 495

Pro Glu Pro Glu Gln Leu
            500

<210> SEQ ID NO 2
<211> LENGTH: 30
<212> TYPE: PRT
<213> ORGANISM: Homo sapiens

<400> SEQUENCE: 2

Gly Pro Pro Ala Ala Ala Pro Gly His Pro Leu Ala Pro Gly Pro His
1               5                   10                  15

Pro Ala Ala Pro Ser Ser Trp Gly Pro Arg Pro Arg Arg Tyr
            20                  25                  30
```